(12) United States Patent
Basu et al.

(10) Patent No.: US 11,986,320 B2
(45) Date of Patent: May 21, 2024

(54) ELECTRODE CONFIGURATIONS FOR DIAGNOSIS OF ARRHYTHMIAS

(71) Applicants: Biosense Webster (Israel) Ltd., Yokneam (IL); Centre Hospitalier Universitaire (CHU) de Bordeaux, Talence (FR); Université de Bordeaux, Bordeaux (FR); Fondation Bordeaux Université, Bordeaux (FR)

(72) Inventors: Shubhayu Basu, Anaheim, CA (US); Meir Bar-Tal, Haifa (IL); Mario A. Solis, Rancho Cucamonga, CA (US); Michel Haissaguerre, Talence (FR); Pierre Jais, Saint Médard en jalles (FR); Meleze Hocini, Pessac (FR); Olivier Bernus, Lacanau de Mios (FR); Rémi Dubois, Mérignac (FR); Masateru Takigawa, Bordeaux (FR)

(73) Assignees: Biosense Webster (Israel) Ltd., Yokneam (IL); Centre Hospitalier Universitaire (CHU) de Bordeaux, Talence (FR); Université de Bordeaux, Bordeaux (FR); Fondation Bordeaux Université, Bordeaux (FR)

(*) Notice: Subject to any disclaimer, the term of this patent is extended or adjusted under 35 U.S.C. 154(b) by 692 days.

(21) Appl. No.: 16/820,848

(22) Filed: Mar. 17, 2020

(65) Prior Publication Data

US 2020/0297281 A1   Sep. 24, 2020

Related U.S. Application Data

(60) Provisional application No. 62/819,738, filed on Mar. 18, 2019.

(51) Int. Cl.
  A61B 5/287 (2021.01)
  A61B 5/00 (2006.01)
  A61B 18/14 (2006.01)

(52) U.S. Cl.
  CPC ............ *A61B 5/6859* (2013.01); *A61B 5/287* (2021.01); *A61B 18/1492* (2013.01); *A61B 2562/04* (2013.01)

(58) Field of Classification Search
  CPC ..... A61B 5/287; A61B 5/6858; A61B 5/6859; A61B 2562/04
  See application file for complete search history.

(56) References Cited

U.S. PATENT DOCUMENTS 5,228,442 A * 7/1993 Imran ................... A61N 1/056
                                                  600/374
5,628,313 A   5/1997 Webster, Jr.
(Continued)

FOREIGN PATENT DOCUMENTS

EP    2923666 A2    9/2015
JP    2015-528352 A  9/2015
(Continued)

OTHER PUBLICATIONS

International Search Report and Written Opinion dated Jul. 14, 2020 for International Application No. PCT/IB2020/000174, 15 pages.
(Continued)

*Primary Examiner* — Eun Hwa Kim
(74) *Attorney, Agent, or Firm* — Frost Brown Todd LLP

(57) ABSTRACT

An apparatus includes a shaft and an end effector at a distal end of the shaft. The end effector is sized to fit in an anatomical passageway within a subject's cardiovascular system. The end effector includes at least one electrode pair that is configured to contact cardiovascular tissue and thereby pick up electrocardiogram signals. Each electrode
(Continued)

pair includes first and second electrodes spaced apart along a longitudinal axis from each other by a gap area located between the electrodes, the gap area having a gap length with respect to the longitudinal axis such that a length of one of the electrodes along the longitudinal axis is equal to or greater than the gap length; and a ratio of an area defined by the gap area to one electrode area is equal to or less than one.

19 Claims, 12 Drawing Sheets

(56) References Cited

U.S. PATENT DOCUMENTS

| | | |
|---|---|---|
| 5,738,096 A | 4/1998 | Ben-Haim |
| 6,123,699 A | 9/2000 | Webster, Jr. |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,210,407 B1 | 4/2001 | Webster |
| 6,267,746 B1 | 7/2001 | Bumbalough |
| 8,364,234 B2 | 1/2013 | Kordis et al. |
| 9,480,416 B2 | 11/2016 | Govari et al. |
| 9,907,480 B2 | 3/2018 | Basu et al. |
| 2016/0100884 A1 | 4/2016 | Fay et al. |
| 2016/0278841 A1 | 9/2016 | Panescu et al. |
| 2017/0000365 A1* | 1/2017 | Wu .................... A61B 18/1492 |
| 2017/0224237 A1* | 8/2017 | Basu ...................... A61B 5/287 |
| 2018/0036078 A1 | 2/2018 | Ditter |
| 2018/0056038 A1 | 3/2018 | Aujla |

FOREIGN PATENT DOCUMENTS

| | | |
|---|---|---|
| JP | 2018-108376 A | 7/2018 |
| WO | WO 2014/031865 A1 | 2/2014 |
| WO | WO 2016/148249 A1 | 9/2016 |

OTHER PUBLICATIONS

Japanese Notification of Reasons for Refusal dated Nov. 7, 2023, for Application No. 2022-504740, 7 pages.

* cited by examiner

ELECTRODE CONFIGURATIONS FOR DIAGNOSIS OF ARRHYTHMIAS

PRIORITY

This application claims priority to U.S. Provisional Pat. App. No. 62/819,738, entitled "Electrode Configurations for Diagnosis of Arrhythmias," filed Mar. 18, 2019, the disclosure of which is incorporated by reference herein in its entirety.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue.

Some catheter ablation procedures especially those with persistent atrial fibrillation may be performed using electrophysiology (EP) mapping to target areas of aberrant electrical signals. Such EP mapping may include the use of sensing electrodes on a catheter (e.g., the same catheter that is used to perform the ablation). Such sensing electrodes may monitor electrical signals within the cardiovascular system to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein. Examples of EP mapping catheters are described in U.S. Pat. No. 9,907,480, entitled "Catheter Spine Assembly with Closely-Spaced Bipolar Microelectrodes," issued Mar. 6, 2018, the disclosure of which is incorporated by reference herein; U.S. Pub. No. 2018/0036078, entitled "Catheter with Soft Distal Tip for Mapping and Ablating Tubular Region," published Feb. 8, 2018, issued as U.S. Pat. No. 10,130,422 on Nov. 20, 2018, the disclosure of which is incorporated by reference herein; and U.S. Pub. No. 2018/0056038, entitled "Catheter with Bipolar Electrode Spacer and Related Methods," published Mar. 1, 2018, issued as U.S. Pat. No. 10,702,177 on Jul. 7, 2020, the disclosure of which is incorporated by reference herein.

In addition to using EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, Calif. Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein; and various other references that are cited herein. All of the documents cited herein are hereby incorporated by reference as if set forth in full herein this application.

While several catheter systems and methods have been made and used, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. Exemplary Mapping Catheter Assembly

A. Overview

Figure 1:
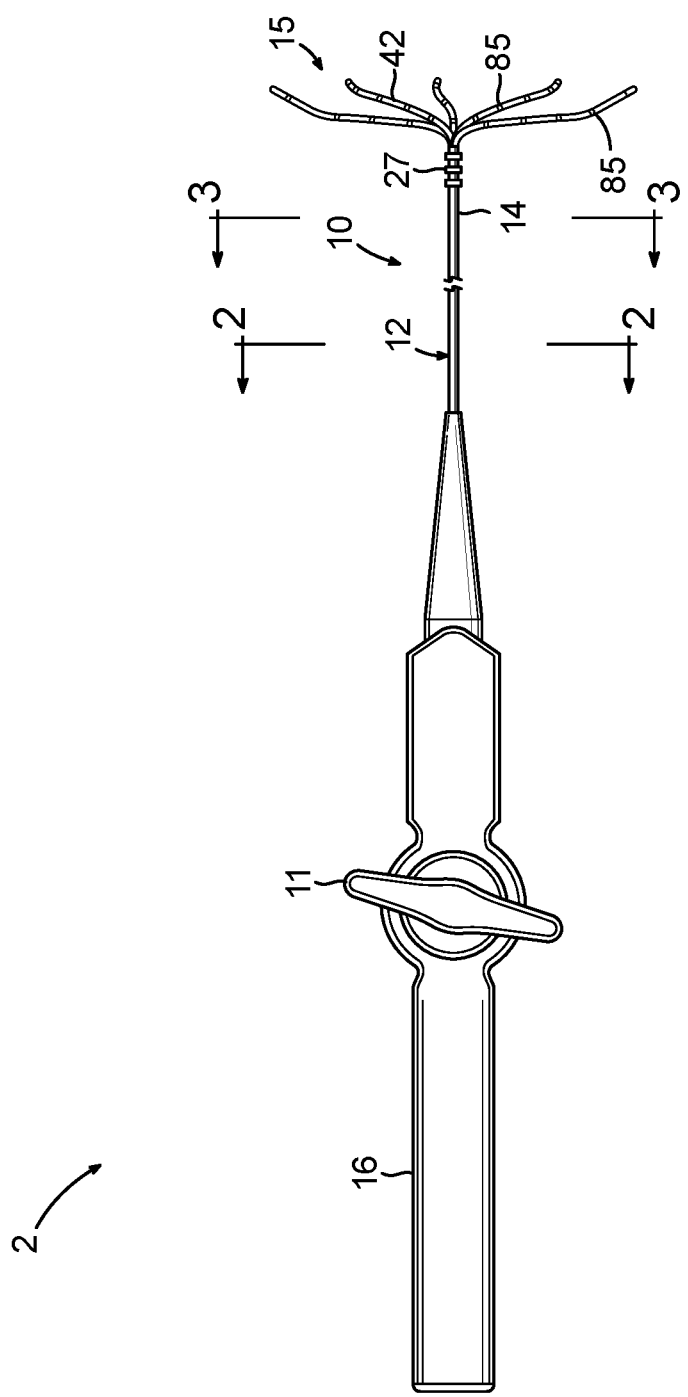
FIG. 1 depicts a top plan view of an exemplary mapping catheter assembly.

FIG. 1 shows an exemplary mapping catheter assembly (2) that may be used to provide EP mapping within the heart or other cardiovascular anatomical structures within a patient. Catheter assembly (2) of this example includes a control handle (16) and a catheter (10) extending distally from control handle (16). Catheter (10) includes a proximal portion (12) and a distal deflection portion (14), which is laterally deflectable relative to proximal portion (12) in response to actuation of a deflection control knob (11) of control handle (16) as will be described in greater detail below. An end effector (15) is positioned at the distal end of catheter (10). As will also be described in greater detail below, end effector (15) includes a plurality of spines (42) having respective free ends, each spine carrying at least one pair of closely-spaced bipolar microelectrodes (85), which are configured to pick up electrocardiogram signals from tissue.

Figure 2:
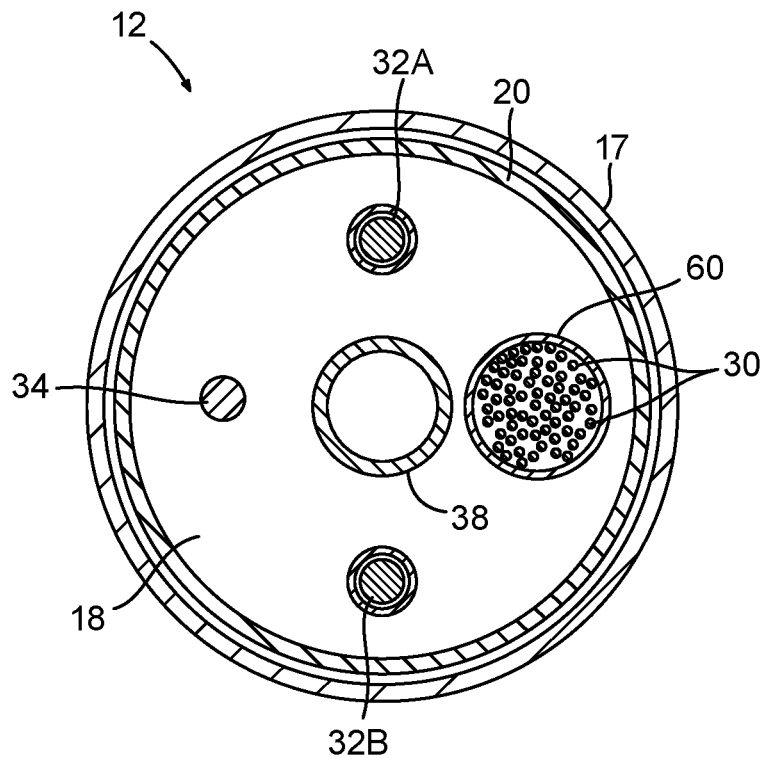
FIG. 2 depicts a cross-sectional end view of the mapping catheter assembly of FIG. 1, taken along line 2-2 of FIG. 1.

In the present example, proximal portion (12) of catheter (10) is flexible but substantially non-compressible along its length. As shown in FIG. 2, proximal portion (12) of catheter (10) includes an outer wall (17) positioned coaxially about a stiffening tube (20). By way of example only, the outer diameter of proximal portion (12) may be less than approximately 8 French. Stiffening tube (20) and outer wall (17) are together configured to provide substantial torsional stability while also providing a minimal wall thickness. Due to the torsional stability provided by stiffening tube (20) and outer wall (17), when control handle (16) is rotated, deflection portion (14) of catheter (10) and end effector (15) will rotate in a corresponding manner. In some variations, stiffening tube (20) is omitted. A lumen (18) extends through the interior of stiffening tube (20). Lumen (18) is sized to accommodate various components, including, for example, one or more puller wires, electrode lead wires, irrigation tubing, and any other wires and/or cables as described below.

Figure 3:
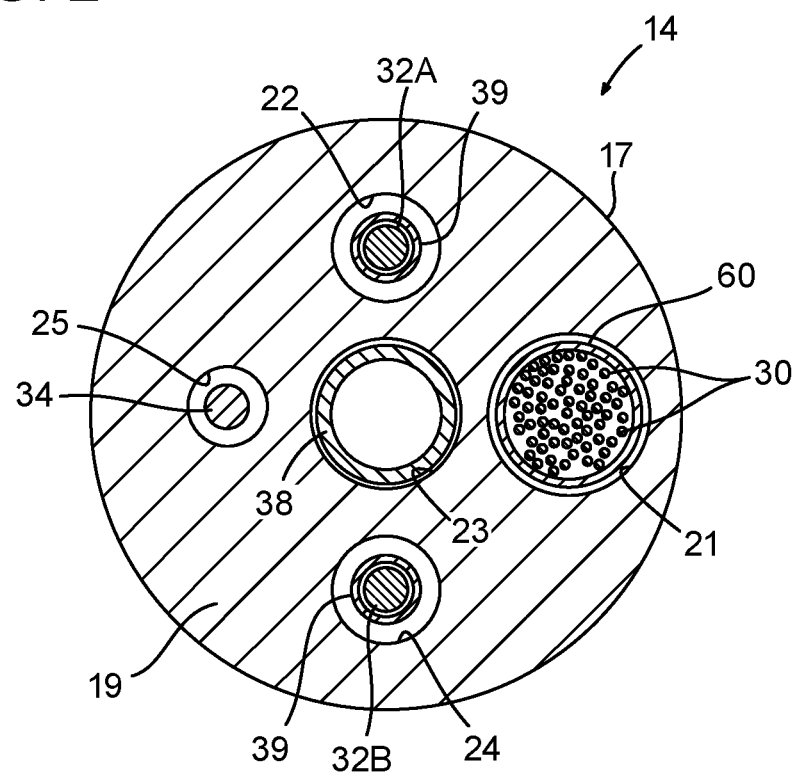
FIG. 3 depicts a cross-sectional end view of the mapping catheter assembly of FIG. 1, taken along line 3-3 of FIG. 1.

As shown in FIG. 3, deflection portion (14) of catheter (10) includes a tube body (19) that defines a central lumen (23) and a plurality of off-axis lumens (21, 22, 24, 25) that are sized to accommodate various components as described below. In the present example, tube body (19) is formed of a material that is more flexible than proximal portion (12) of catheter (10). In the present example, a set of lead wires (30) are contained in a nonconductive sheath (60) and extend through the length of catheter (10). As shown in FIGS. 2-3, lead wires (30) and sheath (60) are positioned in lumens (18, 21). Lead wires (30) are coupled with microelectrodes (85) as will be described in greater detail below. A set of puller wires (32A, 32B) are contained in respective sheaths (39) and extend through the length of catheter (10). Puller wires (32A, 32B) are positioned in lumen (18) and respective lumens (22, 24); and are angularly offset from each other by 180 degrees in the present example. Puller wires (32A, 32B) are operable to provide bi-directional lateral deflection of deflection portion (14) as will be described in greater detail below. A guidewire tube (38) also extends through the length of catheter (10) and is positioned in lumens (18, 23). Guidewire tube (38) is configured to slidably accommodate a conventional guidewire (not shown), which may be used to assist in guiding catheter (10) in various ways as will be apparent to those skilled in the art in view of the teachings herein. A sensor cable (34) also extends through the length of catheter (10) and is positioned in lumens (18, 25). Sensor cable (34) is coupled with an electromagnetic position sensor (36) as will be described in greater detail below.

Figure 4:
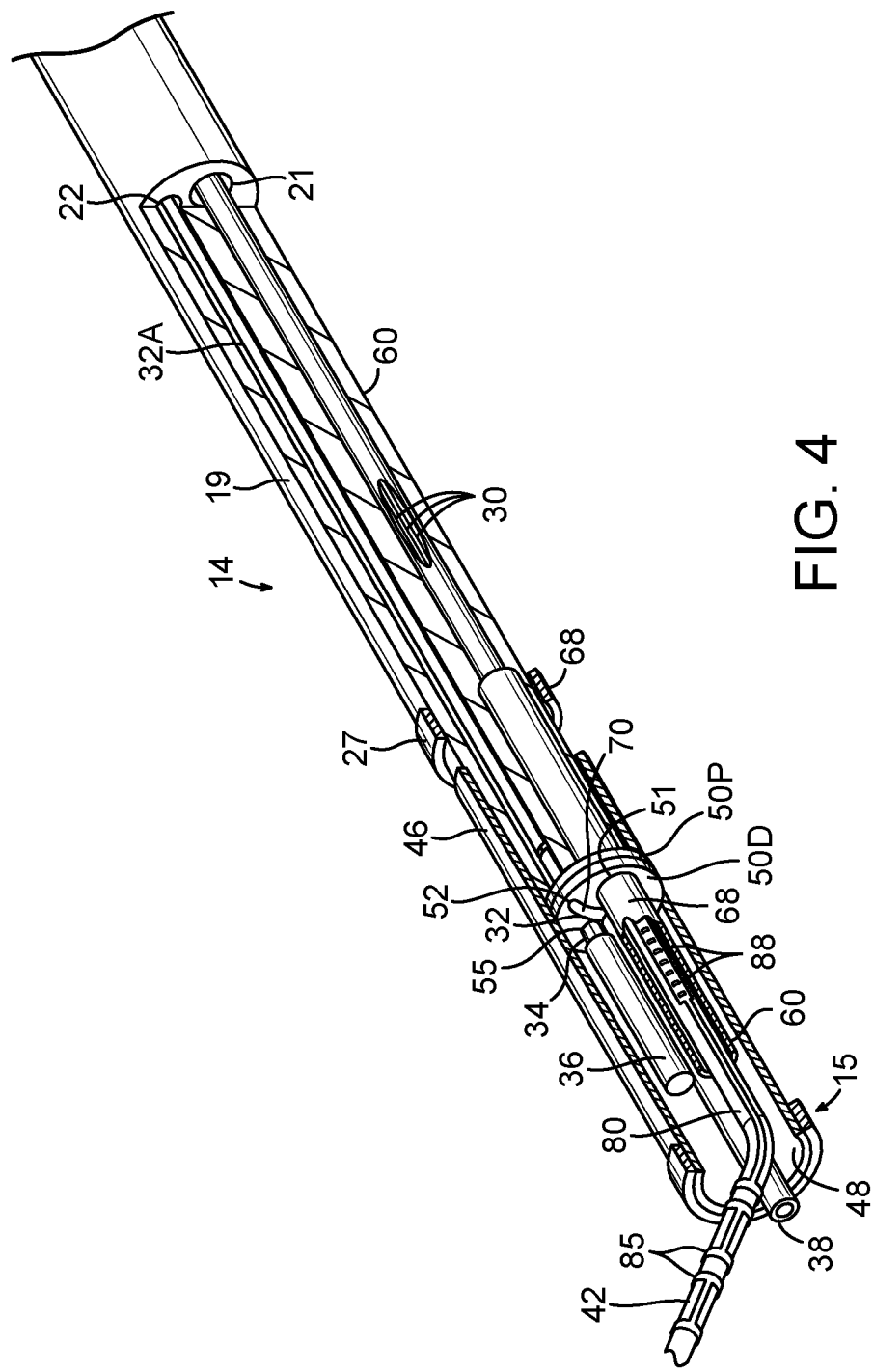
FIG. 4 depicts a perspective, partial cross-sectional view of a distal portion of the mapping catheter assembly of FIG. 1.

As shown in FIG. 4, a mounting stem (46) extends between deflection portion (14) and end effector (15). Stem (46) is in the form of a short tubing mounted on a distal end of tube body (19). Stem (46) has a central lumen (48) to house various components, including position sensor (36) and a distal anchor for puller wires (32A, 32B). In the present example, the distal anchor includes a pair of washers (50D, 50P), each of which has a plurality of through-holes (52, 54) that allow passage of components between deflection portion (14) and stem (46). Through-holes (52, 54) are axially aligned with lumens (22, 24) of tube body (19), respectively, to receive a distal end of puller wires (32A, 32B), respectively. With tension on washers (50D, 50P), exerted by puller wires (32A, 32B), washers (50D, 50P) firmly and fixedly abut against the distal end of tube body (19) of the deflection portion (14). Each washer (50D, 50P) includes through-hole (51) that is axially aligned with lumen (21) and allows passage of lead wires (30) from deflection portion (14) and into lumen (48). Each washer (50D, 50P) also includes through-hole (55) that is axially aligned with lumen (25) and allows passage of sensor cable (34) into lumen (48) where the position sensor (36) is housed. Each washer (50D, 50P) further includes on-axis through-hole (53), which is axially aligned with lumen (23) and allows passage of guidewire tubing (38) into lumen (48).

As shown in FIGS. 3-4, puller wires (32A, 32B) are provided for bi-directional deflection of deflection portion (14). The puller wires (32A, 32B) are actuated by mechanisms in control handle (16) that are responsive to a thumb control knob or a deflection control knob (11) (see FIG. 1). By way of example only, such deflection controls may be provided in accordance with the teachings of any one or more of U.S. Pat. Nos. 6,123,699; 6,171,277; 6,183,435;

6,183,463; 6,198,974; 6,210,407 and 6,267,746, the entire disclosures of which are incorporated herein by reference.

B. Exemplary Multi-Ray End Effector

As shown in FIGS. 1 and 4-9, end effector (15) of mapping catheter assembly (2) includes a set of ring electrodes (27) positioned at the distal end of catheter (10) and a plurality of spines (42), each spine carrying at least one pair of closely-spaced bipolar microelectrodes (85). In the present example, the microelectrodes (85) of a pair has a separation space gap distance therebetween of no greater than about 200 microns. At least one pair of closely-spaced bipolar microelectrodes (85) are provided on each spine (42) in the present example. More particularly, in the present example, each spine (42) carries four pairs of bipolar microelectrodes (85) for a total of eight microelectrodes (85) per spine (42). This number may be varied as desired. By way of example only, end effector (15) may include two to eight spines (42); or more spines (42) as desired. While the spines (42) are shown having respective free ends, other versions may have at least one free end of one spine connect to another free end of another spine with a continuous member.

Figure 5:
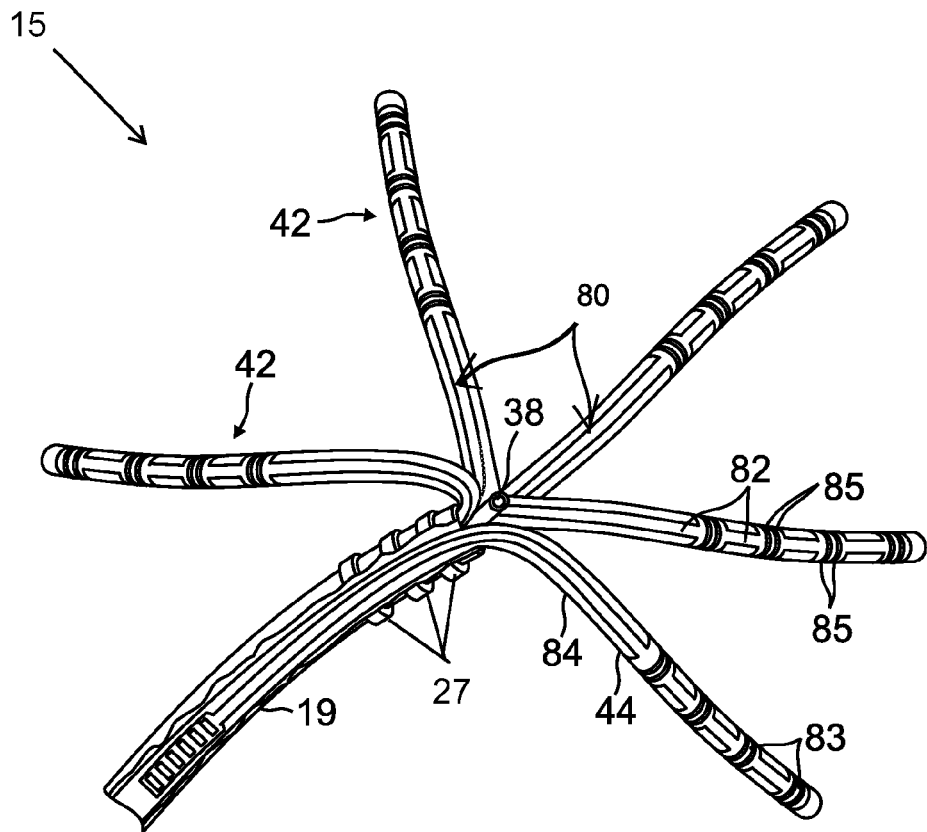
FIG. 5 depicts a perspective view of an end effector of the mapping catheter assembly of FIG. 1, with a portion of a catheter sheath broken away to reveal internal structures.
Figure 6:
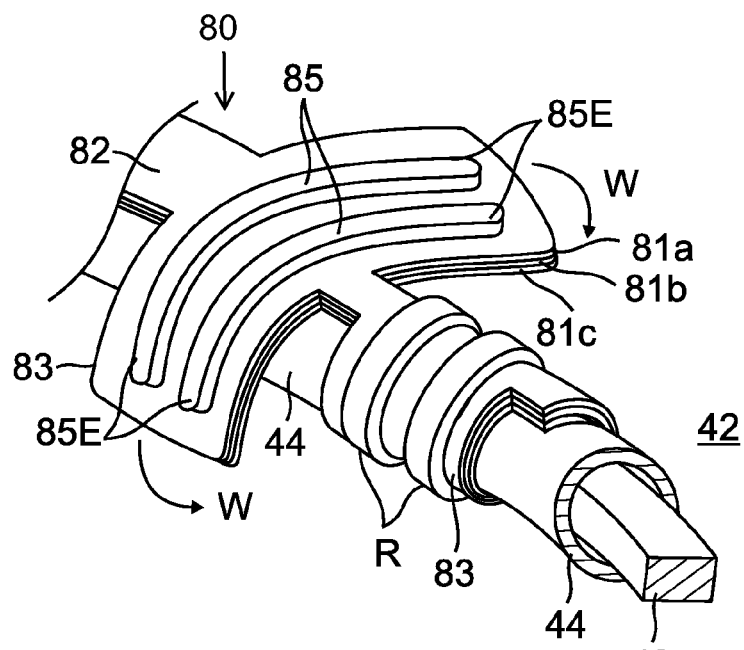
FIG. 6 depicts an enlarged perspective view of an electrode assembly of the end effector of FIG. 5.

As shown in FIGS. 4-6, each spine (42) has a support member (43) and a non-conductive covering (44) that extends along each spine (42). A proximal portion of each spine (42) extends proximally into lumen (48) of stem (46). Spines (42) arranged uniformly about the distal opening of stem (46) in equiangular distances from each other. An adhesive (not shown) seals the distal end of stem (46) around the proximal portions of spines (42); while leaving open the distal end of guidewire tube (38). In the present example, each spine support member (43) is made of a material having shape-memory (e.g., nitinol, etc.). Non-conductive covering (44) can be made of any suitable material, such as a biocompatible plastic (e.g., polyurethane or PEBAX).

Lead wires (30) for microelectrodes (85) carried on the spines (42) extend through both portions (12, 14) of catheter (10) protected by nonconductive sheath (60). Toward end effector (15), lead wires (30) extend through a polytube (68), as shown in FIG. 4. Lead wires (30) diverge at the distal end of polytube (68) and extend toward their respective spine (42). While only one spine (42) is shown in FIG. 4, polytube (68) may be sized appropriately to receive the proximal ends of all spines (42).

Figure 7:
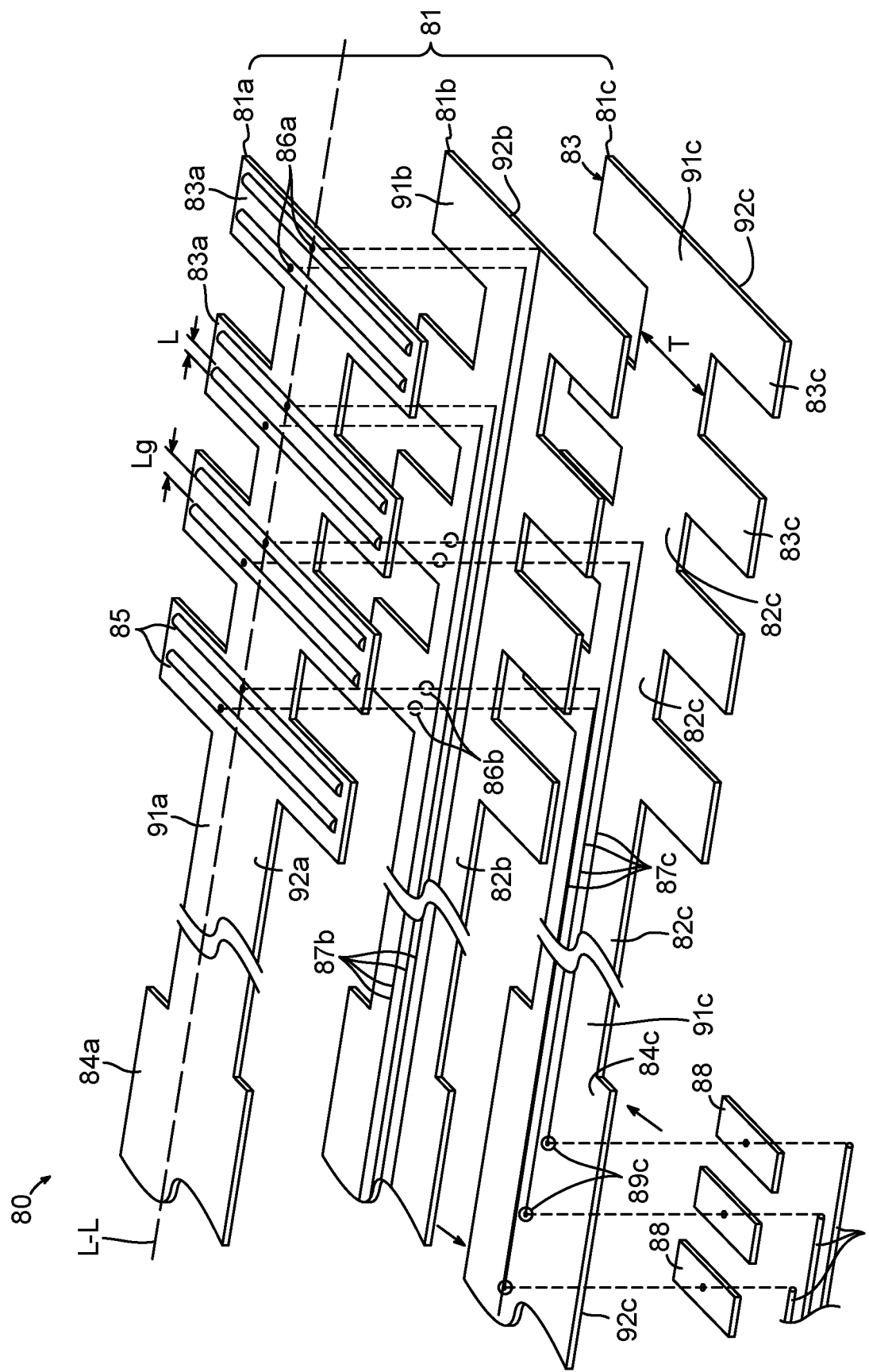
FIG. 7 depicts an exploded view of an electrode assembly of the end effector of FIG. 5.

As shown in FIG. 5 and FIG. 6, each spine (42) includes a flexible microelectrode member in the form of a panel (80) that is affixed to the outer surface of spine (42), conforming to the shape of spine (42). As shown in FIG. 7, panel (80) includes a biocompatible flexible plastic substrate (81) with at least one pair of close-spaced microelectrodes (85), separated therebetween by a non-conducting gap space (Lg). In some versions, substrate (81) is generally elongated with a thinner (T) portion (82), at least one distal wider portion (83) traversing longitudinal portion (82) at a generally perpendicular angle, and a proximal base portion (84a or 84c) having a slightly greater lateral dimension than longitudinal portion (82). Longitudinal portion (82) is configured to extend along the length of spine (42) and lateral portion (83a, 83b, 83c) is configured to wrap circumferentially around a distal portion of spine (42) (R in FIG. 5). Base portion (84a, 84c) is positioned on a proximal end portion of spine (42) and is thus protected within lumen (48). On base portion (84c) are soldering patches (88), one for each lead wire (30) whose distal end is soldered to a respective soldering patch (88). Soldering patches (88) are therefore protected and insulated within lumen (48).

As shown in FIG. 6, microelectrodes (85) (microelectrode strips) are affixed or otherwise provided in alignment with lateral portion (83), on an outer surface of each lateral portion (83), such that each microelectrode (85) generally forms a ring microelectrode (R) when lateral portion (83) is wrapped circumferentially around spine (42). Longitudinal portion (82) may be as wide as lateral portion (83), though the amount of surface area coverage or thickness of the substrate may affect the flexibility of spine (42). Microelectrodes (85) may be made of any suitable solid conductive material, such as platinum or gold, or a combination of platinum and iridium. Some versions of microelectrodes (85) are coated with iridium oxide or are plasma treated to improve the signals to noise characteristics of the microelectrodes.

In some versions, the space gap distance (Lg) separating each microelectrode (85) of a pair ranges from about 50 to about 300 microns. In some versions, the space gap distance (Lg) separating each microelectrode (85) of a pair ranges from about 100 to about 200 microns. In some versions, the space gap distance (Lg) separating each microelectrode (85) of a pair is about 50 microns. Moreover, in some versions, each microelectrode (85) itself may have a width (W) ranging from about 50 microns to about 100 microns. In some versions, panel (80) has a length of about 8.0 cm, wherein longitudinal portion (82) has a length of about 5.0 cm and a width no greater than about 1.0 mm; and base portion (84) has a length of about 3.0 cm and a width of about 1.2 mm. Each pair of microelectrodes (85) is spaced apart from an adjacent pair of microelectrodes (85) by a distance of about 5.0 mm, with each microelectrode (85) having a width of about 50 microns and a length of about 2.56 mm. Other suitable dimensions and arrangements will be described in greater detail below.

As shown in FIG. 7, substrate (81) of the present example is formed of a first or outer layer (81a), a second or middle layer (81b), and a third or inner layer (81c), each having a first surface (91) defined by surfaces (91c, 91b, 91c), and a second surface (92) defined by surfaces (92a, 92b, 92c) that extend along a longitudinal axis L-L. It is understood that the letters "a," "b," and "c" designate corresponding features in layers (81a, 81b 81c) of the substrate (81). Microelectrodes (85) are applied to or otherwise deposited on first surface (91a) of outer layer (81a) to overlie through-holes (86a), which are formed in layer (81a) to provide connection access for electrical traces (87b) that extend along first surface (91b) of longitudinal portion (82b) of second layer (81b) between corresponding microelectrodes (85) and soldering pads (88) carried on second surface (92c) of base portion (84c) of the third layer (81c). Additional traces (87c) run along first surface (91c) of third layer (81c). Through-holes (86b, 89b, 89c) are formed in layers (81b, 81c) to provide connection access for electrical traces (87b, 87c) to more proximal microelectrodes (85) and more proximal soldering pads (not shown in FIG. 7).

In the present example, substrate (81) has three layers with each layer (81a, 81b, 81c) carrying four traces (87). It is understood that there is one corresponding trace (87) and one corresponding soldering pad (88) for each microelectrode (85) in this example. Each lead wire (30) is soldered to a corresponding soldering pad (88). In that regard, it is also understood that traces (87) may be arranged differently, in different patterns, and/or on different layers (81), as needed or appropriate. Adjacent microelectrodes (85) are separated by a space (Lg) and each microelectrode (85) may have a width (W) having the dimensions noted earlier and defined later in FIG. 13A.

As shown in FIG. 5 and FIG. 6, substrate (81) is affixed to nonconductive covering (44) of the spine (42) with the longitudinal portion (82) extending longitudinally along spine (42) and lateral portions (83) wrapped circumferentially around spine (42). In that regard, the lateral dimension or width (W) as referenced to longitudinal axis L-L of lateral portions (83), and more significantly of microelectrodes (85), is comparable to the circumference of spine (42) such that opposing ends (85E) of microelectrodes (85) can reach each other or at least come in close contact to generally form and function as ring microelectrodes (R) carried on spine (42). In the present example, substrate (81) is affixed to the forward-facing or distal side of the spine (42) that is adapted to contact tissue.

Figure 8:
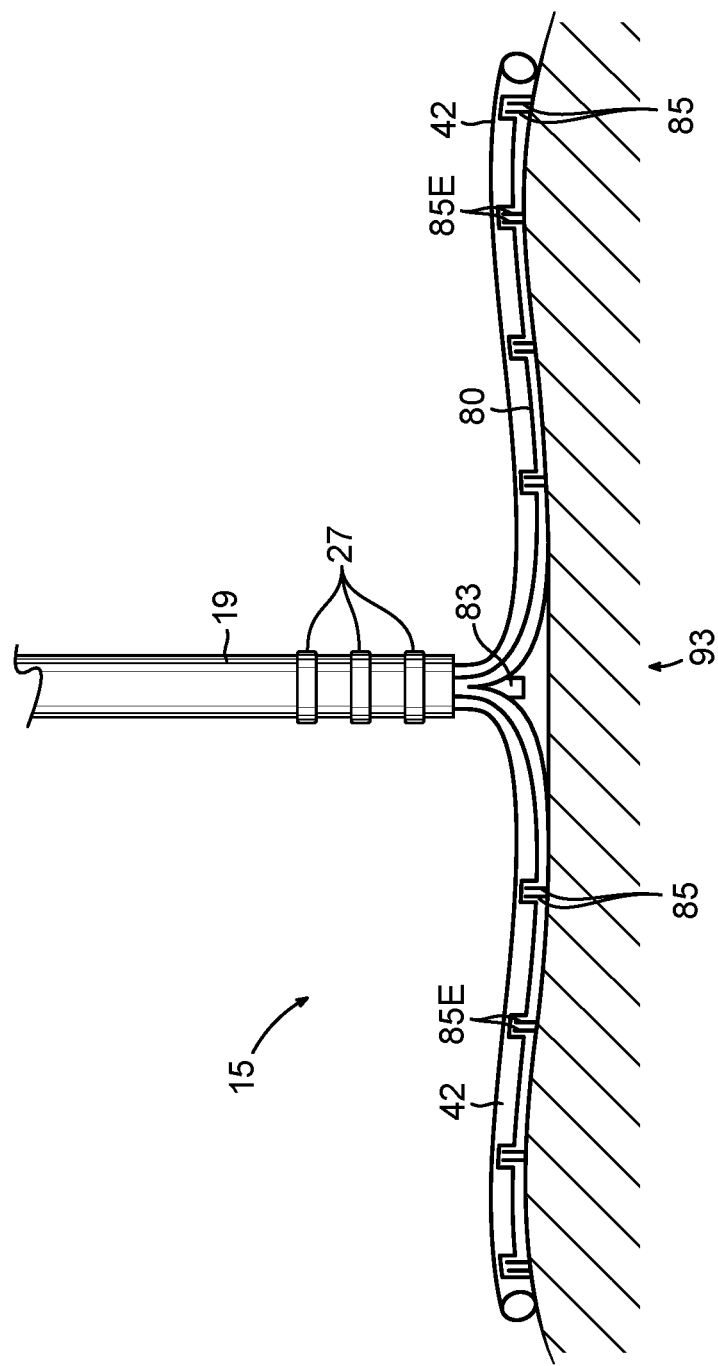
FIG. 8 depicts a side schematic view of the end effector of FIG. 5 contacting a tissue surface.

As shown in FIG. 5, each spine (42) is pre-formed with a slight inward curvature such that end effector (15) has a generally slightly concave configuration resembling an open umbrella. This preformed configuration enables each spine (42) to engage a tissue surface (93) generally along its entire length when end effector (15) is advanced distally against the tissue surface (93), as shown in FIG. 8.

Figure 9:
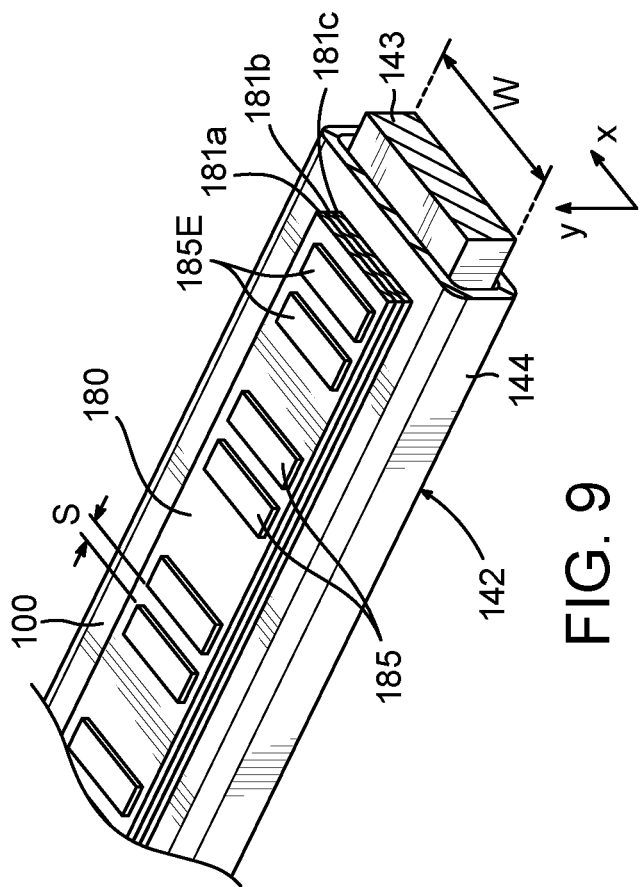
FIG. 9 depicts a partial perspective view of another exemplary electrode assembly that may be incorporated into the end effector of FIG. 5.
Figure 10:
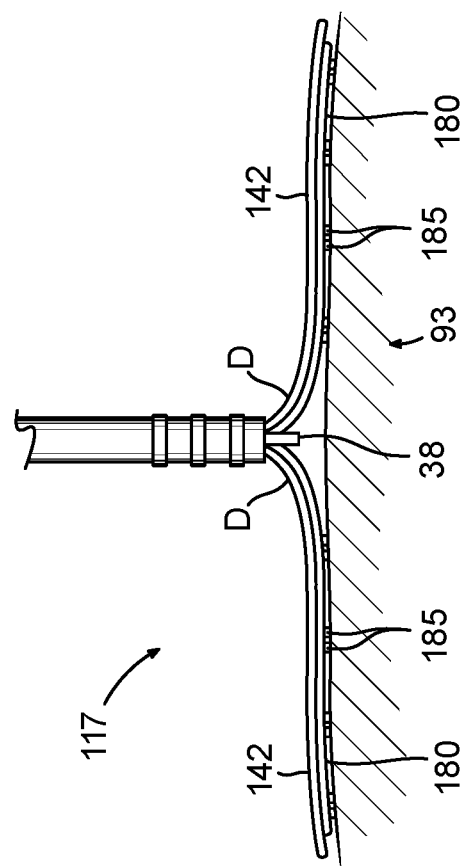
FIG. 10 depicts a side schematic view of the end effector of FIG. 5 incorporating the electrode assembly of FIG. 9, contacting a tissue surface.

FIGS. 9-10 show components of another exemplary multi-ray end effector (117) that may be incorporated into mapping catheter assembly (2) in place of end effector (15) in which each spine (142) defines a longitudinal axis L-L. Alternatively, end effector (117) may be incorporated into various other kinds of mapping catheter assemblies. End effector (117) of this example includes a plurality of spines (142) with pairs of microelectrodes (185) mounted thereon. Whereas spine (42) of FIG. 6 has a more circular cross-section, spine (142) of FIG. 9 has a more rectangular cross section, which provides the greater planar surface (100) on which a flexible microelectrode member in the form of a panel (180) can be selectively applied or affixed. Advantageously, the entirety of microelectrodes (185) (including their ends (180E)) is confined to the surface area of planar surface (100). Spines (142) thus have microelectrodes (185) on only one side of each spine (142) (i.e., the tissue-contacting side of each spine (142)). Therefore, generally the entirety of microelectrodes (185) is in contact with tissue (193) when planar surface (100) is in contact with tissue (193), as shown in FIG. 10. Having spines (142) with a rectangular cross-section wherein the X dimension along the planar surface (100) and transverse to the L-L axis is greater than the Y dimension perpendicularly to the X dimension, as shown in FIG. 9, may help minimize kinking and stress to spines (142) at their area of greatest flexion or divergence (D) (see FIG. 10).

Support member (143) has a rectangular cross-section which is adopted by heat-shrink nonconductive covering (144) to provide the greater planar surface (100). Substrate (181) of panel (180) comprises multiple layers (181a, 181b, 181c) in the present example. However, substrate (181) is devoid of lateral portions, with a longitudinal portion having a lateral dimension (W) that is comparable or at least no greater than the lateral dimension of planar surface (100) so that substrate (181) remains confined on planar surface (100). Microelectrodes (185) are elongated and thin, with a rectangular shape in this example. Microelectrodes (185) may be made of any suitable solid conductive material, such as platinum or gold, or a combination of platinum and iridium. Some versions of microelectrodes (185) are coated with iridium oxide or are plasma treated.

As noted above, end effector (15) includes a position sensor (36). Position sensor (36) is operable to generate signals that are indicative of the position and orientation of end effector (15) within the patient. In some versions, position sensor (36) includes a wire coil or a plurality of wire coils (e.g., three orthogonal coils) that are configured to generate electrical signals in response to the presence of an alternating electromagnetic field generated by field generators that are positioned near the patient. Such position sensing capabilities may be provided in accordance with the teachings of any of the various patent references cited herein. End effector (117) may also include a position sensor (36) or variations thereof. Other components and techniques that may be used to generate real-time position data associated with end effector (15, 117) may include wireless triangulation, acoustic tracking, optical tracking, inertial tracking, and the like. Alternatively, position sensing capabilities may be omitted from end effector (15, 117).

In an exemplary use, catheter (10) may be inserted into a patient's cardiovascular system (e.g., via a femoral artery, etc.), with deflection control knob (11) and deflection portion (14) being used to steer end effector (15, 117) to a desired location (e.g., in or near a pulmonary vein, etc.). In some versions, an outer sheath (not shown) may be positioned about end effector (15, 117) to constrain spines (42) as end effector (15, 117) is advanced to the target location. In such versions, the outer sheath may be retracted after end effector (15, 117) reaches or nears the target location. This positioning may be performed with assistance from an image guided surgical system that is in communication with position sensor (36) using known techniques. Once end effector (15, 117) reaches the target location, microelectrodes (85, 185) may be placed in contact with the cardiovascular tissue to obtain electrocardiogram signals. The multi-ray configuration of end effector (15, 117) may enable several electrocardiogram signals to be picked up simultaneously from various regions of anatomy within the cardiovascular space. These electrocardiogram signals may be used to provide EP mapping, to thereby pinpoint the location(s) of aberrant conductive tissue sites that are responsible for cardiac arrhythmia. Once these aberrant conductive tissue sites are identified, the EP map data can be used to guide an ablation catheter to ablate the tissue to thereby treat the arrhythmia.

C. Exemplary Basket End Effector

Figure 11:
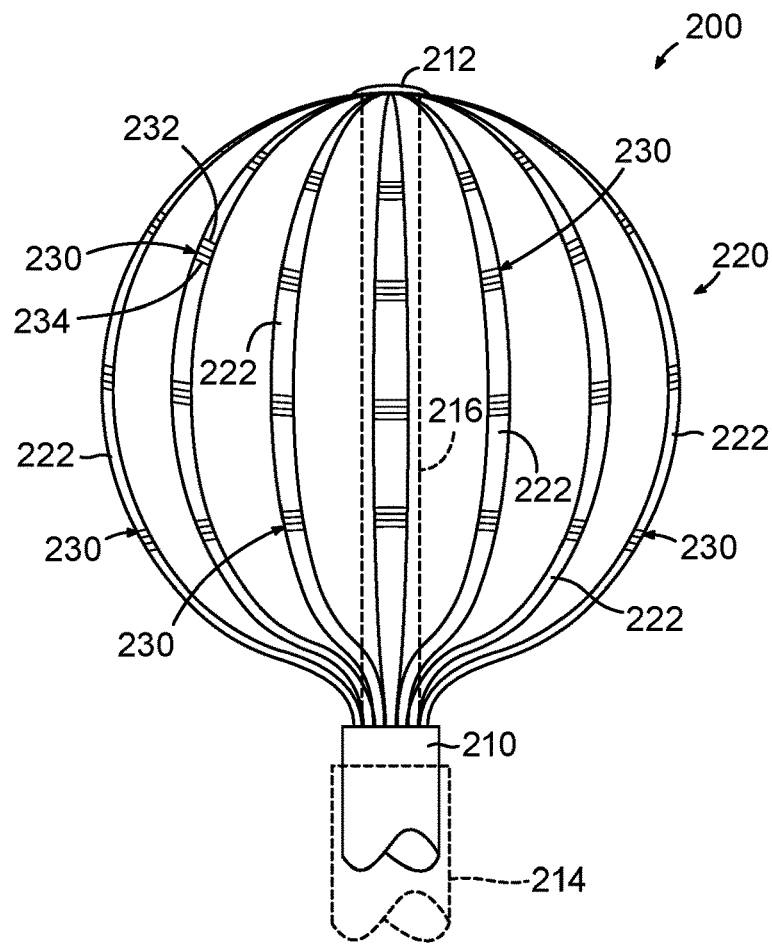
FIG. 11 depicts a side elevation view of another exemplary end effector that may be incorporated into the mapping catheter assembly of FIG. 1.

FIG. 11 shows another exemplary end effector (200) that may be incorporated into mapping catheter assembly (2) in place of end effector (15). Alternatively, end effector (200) may be incorporated into various other kinds of mapping catheter assemblies. End effector (200) of this example includes an expandable assembly (220) that is formed by an angularly spaced array of beams (222). Each beam (222) includes four pairs (230) of bipolar microelectrodes (232, 234). Microelectrodes (232, 234) are each generally rectangular and are configured to pick up electrocardiogram signals from tissue, just like microelectrodes (85, 185) described above. Microelectrodes (232, 234) may be made of any suitable solid conductive material, such as platinum or gold, or a combination of platinum and iridium. Some versions of microelectrodes (232, 234) are coated with iridium oxide or are plasma treated. The entirety of each microelectrode (232, 234) is confined to the outwardly presented surface of each beam (222) in the present example. Beams (222) thus have microelectrodes (232, 234) on only one side of each beam (222) (i.e., the tissue-contacting side of each beam (222)). Except as otherwise described herein, the various features of end effector (200) may be configured and operable like end effectors (15, 117) described above.

The proximal ends of beams (222) are positioned in an outer shaft (210), which may be considered as being analogous to mounting stem (46) described above. The distal ends of beams (222) are coupled with a hub member (212). In some versions, hub member (212) is secured to a central inner shaft (216), which is coaxially positioned at the center of expandable assembly (220). Beams (222) are configured to transition expandable assembly (220) between a non-expanded state and an expanded state. The expanded state is shown in FIG. 11. When expandable assembly (220) is in the non-expanded state, beams (222) are urged inwardly to define an effective outer diameter that is less than or equal to the inner diameter of outer shaft (210). In some versions, beams (222) are resiliently biased to provide expandable assembly (220) in the expanded state. In some such versions, an outer sheath (214) is slidably disposed about outer shaft (210). When sheath (214) is in a distal position (e.g., such that the distal end of sheath (214) is distal to hub member (212)), sheath (214) constrains beams (222) inwardly, thereby maintaining expandable assembly (220) in the non-expanded state. When sheath (214) is in a proximal position (e.g., as shown in FIG. 11, such that the distal end of sheath (214) is proximal to expandable assembly (220)), beams (222) may resiliently provide expandable assembly (220) in the expanded state. In versions where beams (222) are resiliently biased to provide expandable assembly (220) in the expanded state, inner shaft (216) may be omitted.

As another merely illustrative alternative, the state of expandable assembly (220) may be based on the relative longitudinal positioning of inner shaft (216) and outer shaft (210). In versions where inner shaft (216) is longitudinally stationary relative to control handle (16), an actuator on control handle (16) may drive outer shaft (210) proximally relative to inner shaft (216) to urge expandable assembly (220) to the non-expanded state; and drive outer shaft (210) distally relative to inner shaft (216) to urge expandable assembly (220) to the expanded state. In versions where outer shaft (210) is longitudinally stationary relative to control handle (16), an actuator on control handle (16) may drive inner shaft (216) distally relative to outer shaft (210) to urge expandable assembly (220) to the non-expanded state; and drive inner shaft (216) proximally relative to inner shaft (210) to urge expandable assembly (220) to the expanded state. Various suitable forms of inputs that may be provided on control handle (16) to provide such actuation, as well as various suitable ways in which expandable assembly (220) may transition between the non-expanded state and the expanded state, will be apparent to those skilled in the art in view of the teachings herein.

In an exemplary use, catheter (10) may be inserted into a patient's cardiovascular system (e.g., via a femoral artery, etc.), with deflection control knob (11) and deflection portion (14) being used to steer end effector (200) to a desired location (e.g., in or near a pulmonary vein, etc.). As end effector (200) is advanced to the target location, expandable assembly (220) may be maintained in the non-expanded state in accordance with the teachings herein. After end effector (200) reaches or nears the target location, expandable assembly (220) may be transitioned to the expanded state in accordance with the teachings herein. In versions where end effector (200) includes a position sensor like position sensor (36), the positioning of end effector (200) may be performed with assistance from an image guided surgical system that is in communication with the position sensor. Once end effector (200) reaches the target location, microelectrodes (232, 234) may be placed in contact with the cardiovascular tissue to obtain electrocardiogram signals. The basket-shaped configuration of end effector (200) may enable various electrode pairs (230) to contact various regions of tissue simultaneously, thereby enabling end effector (200) to pick up several electrocardiogram signals simultaneously from various regions of anatomy within the cardiovascular space. These electrocardiogram signals may be used to provide EP mapping, to thereby pinpoint the location(s) of aberrant conductive tissue sites that are responsible for cardiac arrhythmia. Once these aberrant conductive tissue sites are identified, the EP map data can be used to guide an ablation catheter to ablate the tissue to thereby treat the arrhythmia.

D. Exemplary Balloon End Effector

Figure 12:
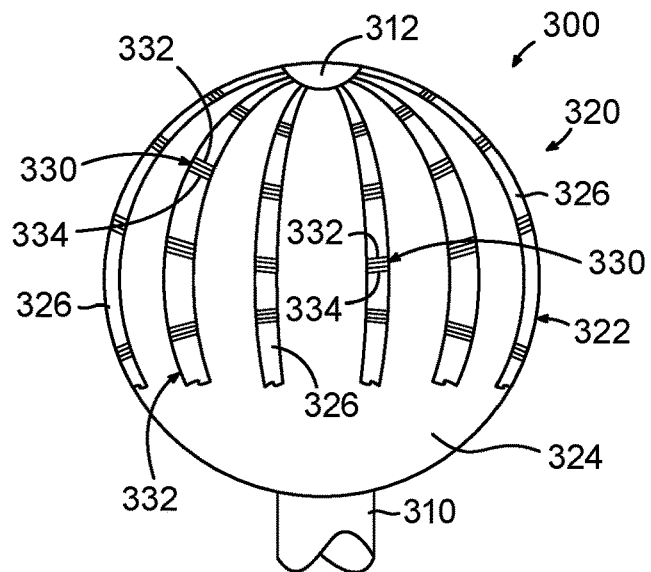
FIG. 12 depicts a side elevation view of another exemplary end effector that may be incorporated into the mapping catheter assembly of FIG. 1.

FIG. 12 shows another exemplary end effector (300) that may be incorporated into mapping catheter assembly (2) in place of end effector (15). Alternatively, end effector (300) may be incorporated into various other kinds of mapping catheter assemblies. End effector (300) of this example includes an expandable assembly (320) that is formed by an expandable balloon (324) with a plurality of flex circuits (322) secured thereto. Flex circuits (322) are positioned in an angularly spaced array about balloon (324). Each flex circuit (322) includes a flexible substrate (326) with four pairs (330) of bipolar microelectrodes (332, 334). Microelectrodes (332, 334) are each generally rectangular and are configured to pick up electrocardiogram signals from tissue, just like microelectrodes (85, 185) described above. Microelectrodes (332, 334) may be made of any suitable solid conductive material, such as platinum or gold, or a combination of platinum and iridium. Some versions of microelectrodes (332, 334) are coated with iridium oxide or are plasma treated. The entirety of each microelectrode (332, 334) is confined to the outwardly presented surface of each flexible substrate (326) in the present example. Flexible substrates (326) thus have microelectrodes (332, 334) on only one side of each flexible substrate (326) (i.e., the tissue-contacting side of each flexible substrate (326)). Except as otherwise described herein, the various features of end effector (300) may be configured and operable like end effectors (15, 117) described above.

The proximal ends of flex circuits (322) terminate distal to the proximal end of balloon (324). The distal ends of flex circuits (322) are joined at a hub (312), which is positioned at a distal end of balloon (324). Balloon (324) is positioned at the distal end of an outer shaft (310), which may be considered as being analogous to mounting stem (46) described above. Balloon (324) is in fluid communication with a source of inflation fluid (e.g., saline, etc.), such that the inflation fluid may be driven into balloon (324) to transition balloon (324) to the inflated state, thereby providing expandable assembly (320) in the expanded state (as shown in FIG. 12). The inflation fluid may be drawn from balloon (324) to transition balloon (324) from the inflated state to the non-inflated state, thereby transitioning expandable assembly (320) to the non-expanded state. In some versions, a central shaft (not shown) is positioned in balloon (324) to maintain consistent spacing between hub (312) and the distal end of outer shaft (310), regardless of expandable assembly (320) is in the expanded or non-expanded state. Various suitable ways in which balloon (324) may be inflated and deflated will be apparent to those skilled in the art in view of the teachings herein.

In an exemplary use, catheter (10) may be inserted into a patient's cardiovascular system (e.g., via a femoral artery, etc.), with deflection control knob (11) and deflection portion (14) being used to steer end effector (300) to a desired location (e.g., in or near a pulmonary vein, etc.). As end effector (300) is advanced to the target location, expandable assembly (300) may be maintained in the non-expanded state in accordance with the teachings herein. After end effector (300) reaches or nears the target location, expandable assembly (320) may be transitioned to the expanded state in accordance with the teachings herein. In versions where end effector (300) includes a position sensor like position sensor (36), the positioning of end effector (300) may be performed with assistance from an image guided surgical system that is in communication with the position sensor. Once end effector (300) reaches the target location, microelectrodes (332, 334) may be placed in contact with the cardiovascular tissue to obtain electrocardiogram signals. The bulbous configuration of end effector (300) may enable various electrode pairs (330) to contact various regions of tissue simultaneously, thereby enabling end effector (300) to pick up several electrocardiogram signals simultaneously from various regions of anatomy within the cardiovascular space. These electrocardiogram signals may be used to provide EP mapping, to thereby pinpoint the location(s) of aberrant conductive tissue sites that are responsible for cardiac arrhythmia. Once these aberrant conductive tissue sites are identified, the EP map data can be used to guide an ablation catheter to ablate the tissue to thereby treat the arrhythmia.

II. Exemplary Microelectrode Configurations for Mapping Catheter End Effector

In some conventional EP mapping instruments, such as conventional mapping catheters with electrodes as are known in the art, the electrocardiogram signals picked up by the electrodes may include a large amount if not a majority of far field signals generated from cardiovascular structures that are not the particular structure being targeted by the microelectrodes. For instance, a physician may place microelectrodes in contact with tissue in the heart (such as, for example, the pulmonary vein) to detect electrocardiogram signals at the site in the heart. In some such instances, the atria of the patient's heart may be generating electrocardiogram signals having a greater amplitude than those of the site (e.g., at pulmonary vein), and those electrocardiogram signals may be picked up by the microelectrodes at the pulmonary vein as far field signals. Other regions of cardiac tissue may also communicate far field signals that are picked up by microelectrodes at the pulmonary vein (or microelectrodes that are placed elsewhere within the cardiovascular space, at some distance from the cardiac tissue generating the far field signals). These far field signals are added to the near-field component and may ultimately yield an electrocardiogram signal that is artificially complex and fractionated, and therefore difficult to interpret.

Figure 14:
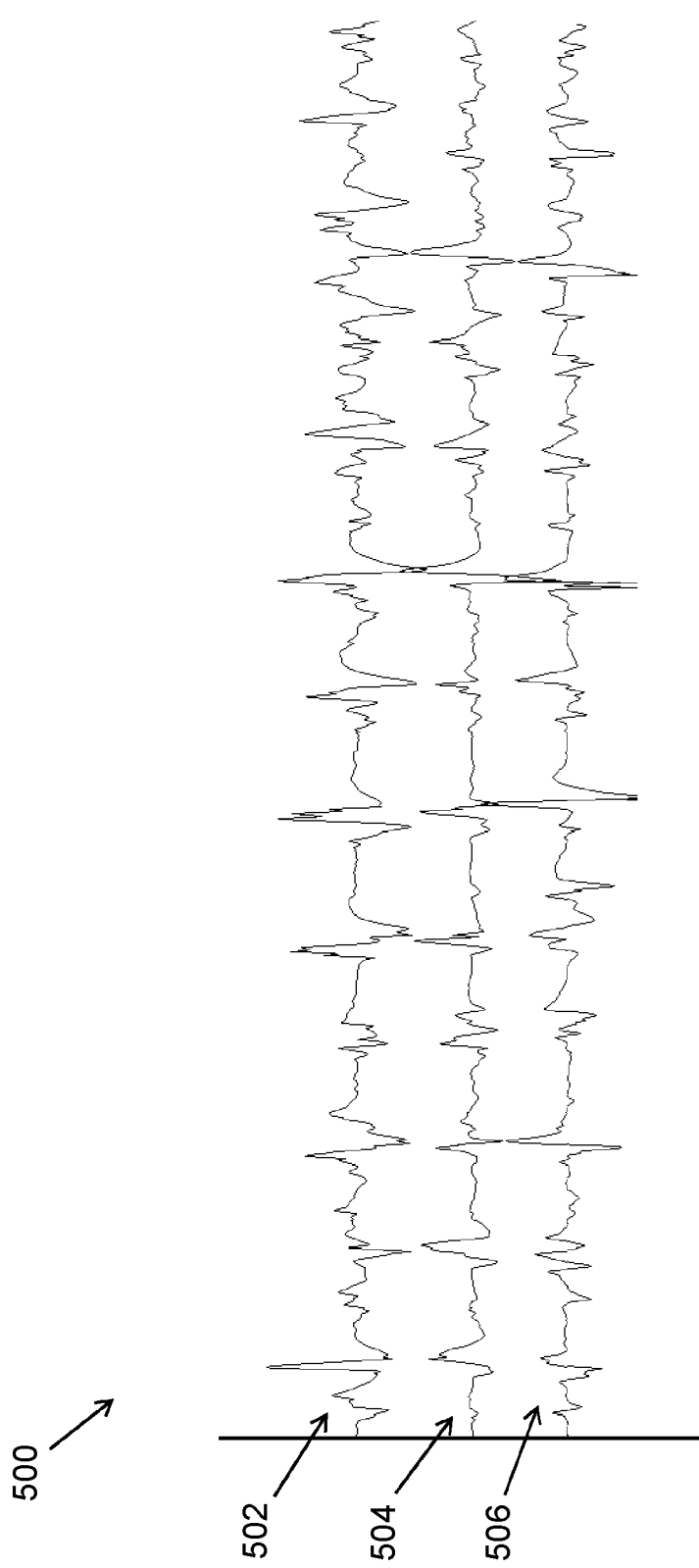
FIG. 14 depicts a plot of electrocardiogram signals showing fractionation.

FIG. 14 shows a graph (500) of three electrocardiogram signal plots from a subject in atrial fibrillation (502, 504, 506) that are fractionated due to the fibrillatory nature of the signal as well as far field signals. Those skilled in the art will understand that plots (502, 504, 506) show voltages over time, as sensed by microelectrodes contacting tissue. By way of example only, plots (502, 504, 506) may represent electrocardiogram signals picked up by three different microelectrode pairs that are positioned within the heart of the patient,). To the extent that the physician is checking the electrocardiogram signals in order to identify particular locations within the pulmonary vein or in any part of the cardiac tissue that are generating aberrant electrical signals (to therefore identify target locations for ablation or other therapy), the fractionation that is shown in plots (502, 504, 506) may make it substantially difficult to identify and correctly annotate the timing and cadence of the polarization/depolarization cycle occurring within the tissue. In other words, it may be difficult for the physician to discriminate between relatively small, close potentials (e.g., from the local tissue) and farther potentials. These are key aspects of electrophysiology ablation procedures as targets for ablation are based on the analysis of the electrical signals recorded by the catheters. The inventors have devised the microelectrodes described and illustrated herein to provide electrocardiogram signals that are substantially free from signal fractionation that is routinely seen in atrial fibrillatory substrate of the patient. This particular kind of signal fractionation should not be confused with noise generated by electrical devices that are external to the patient (e.g., equipment in the operating room, mobile phones, Wi-Fi signals, etc.). The signal fractionation addressed herein is due to signals generated in cardiac tissue within the patient—not noise or other electrical signals generated by man-made equipment or devices that are located internal or external to the patient. Indeed, such fractionation may be found in electrocardiogram signals even if the patient were to be placed in an environment that is free of noise or other electrical signals generated by man-made equipment or devices that are located internal or external to the patient.

To the extent that software or other forms of signal processing may purport to address fractionation from signals generated in cardiac tissue within the patient, such software or other forms of signal processing may be considered unreliable by physicians. Thus, the inventors have devised an electrode-based solution to obtain electrocardiogram signals that are substantially free from fractionation caused by atrial fibrillation and also by the interaction of complex wavefronts in a fibrillatory substrate of a persistent AF patient. Multiple mechanisms have been identified or suspected to generate fractionated electrical signals. This includes wave-front collision, anisotropy, fibrosis, pivoting waves etc. . . . Whatever the mechanism the vast majority of fractionation is due to the fact that the electrodes are sensing signals beyond the tissue they are directly in contact with. The following describes some examples of microelectrodes configurations and arrangements that may provide electrocardiogram signals that are substantially free from fractionation caused by far field signals that are generated within the cardiovascular system of the patient, without requiring additional software or other signal processing solutions that are intended to reduce fractionation caused by far field signals that are generated within the cardiovascular system of the patient.

The following description relates to various arrangements and configurations that may be used for microelectrodes (85, 185, 232, 234, 332, 334) of any of the end effectors (15, 117, 200, 300) described herein. For shorthand purposes, and with reference to FIG. 13, microelectrodes (85, 185, 232, 234, 332, 334) will collectively hereafter be referred to as microelectrodes (402, 404) of a pair (400). The following teachings should be understood as being applicable to all pairs (220, 320) of microelectrodes (85, 185, 232, 234, 332, 334) described above. Those skilled in the art should also recognize that the following teachings may be readily applied to various other kinds of electrodes in various other kinds of instruments, such that the teachings below are not necessarily limited to microelectrodes (85, 185, 232, 234, 332, 334) described above.

Figure 13A:
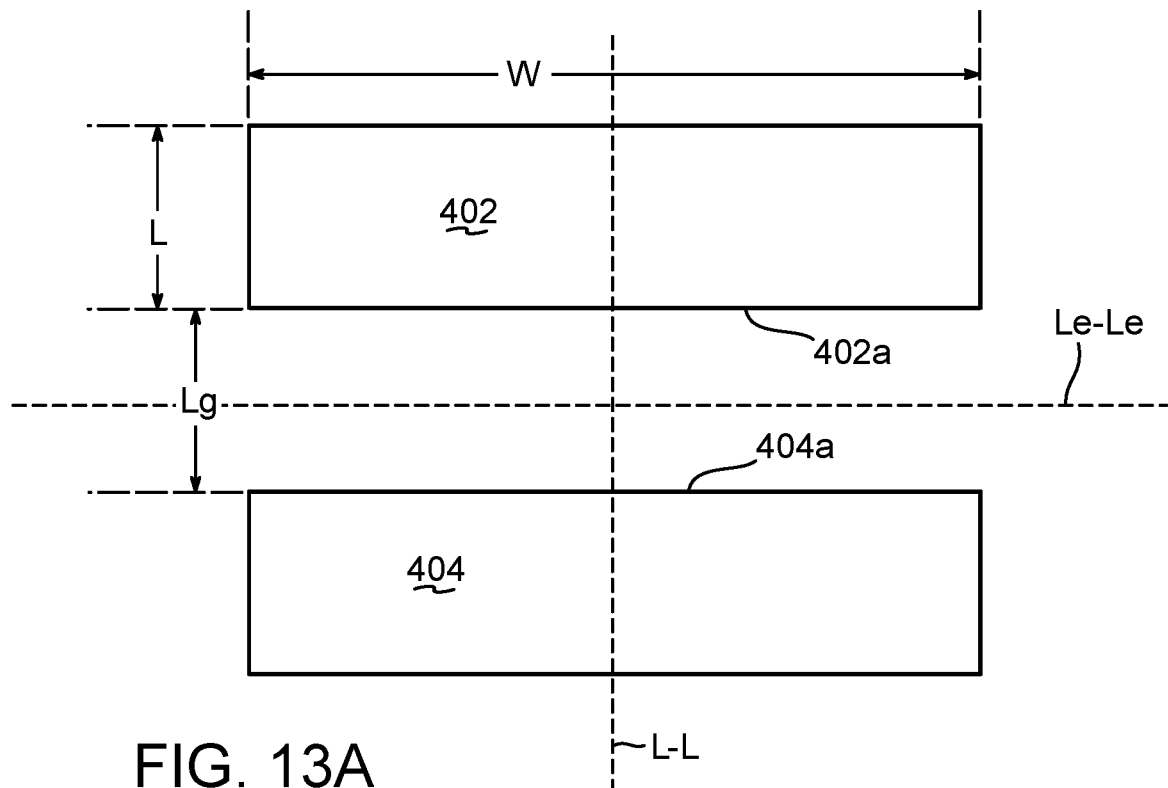
FIG. 13A depicts a schematic view of a pair of rectilinear electrodes that may be incorporated into an end effector of the mapping catheter assembly of FIG. 1.
Figure 13B:
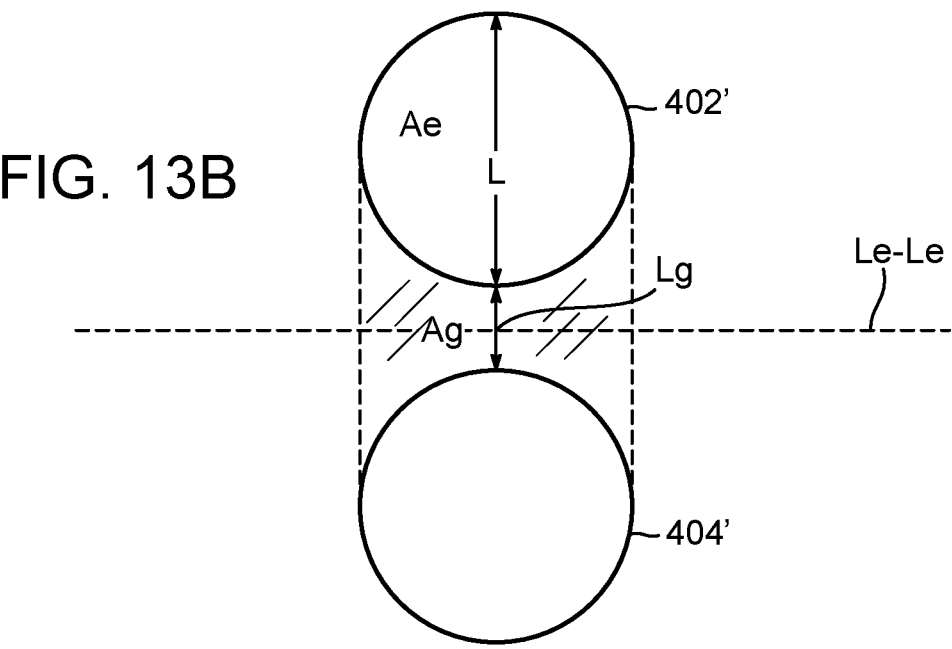
FIG. 13B depicts a schematic plan view of a pair of curvilinear electrodes that may be incorporated into an end effector of the mapping catheter assembly of FIG. 1.

FIG. 13A shows microelectrodes (402, 404) as each having a width (W) and length (L), with a gap (Lg) separating microelectrodes (402, 404). In the present example, the width (W) of microelectrode (402) is equal to the width (W) of microelectrode (404); and the length (L) of microelectrode (402) is equal to the length (L) of microelectrode (404). Microelectrodes (402, 404) thus both have the same surface area (l*w) in the present example. Microelectrodes (402, 404) are oriented parallel to each other so that the two nearest substantially parallel surfaces (402a, 404a) define a longitudinal axis Le-Le for the microelectrode pair such as shown exemplarily in FIGS. 13A, 13C and 13D. In a preferred embodiment, shown in FIG. 13A, the microelectrodes (402, 404) are arranged such that the length (L) extends parallel to the longitudinal axis L-L of the structure to which microelectrodes (402, 404) are mounted (e.g., spines (42, 142), beams (222), flexible substrates (326), etc.); and such that the width (W) extends generally parallel to electrodes' longitudinal axis Le-Le or generally perpendicular to the longitudinal axis L-L of the structure to which microelectrodes (402, 404) are mounted. Microelectrodes (402, 404) are positioned such that microelectrodes (402, 404) are spaced apart from each other along the length of the structure to which microelectrodes (402, 404), such that the gap (Lg) extends between the two nearest surfaces (402a, 404a) of the microelectrodes. For convenience of nomenclature with respect to this embodiment, the gap (Lg) is also taken to be substantially parallel to the longitudinal axis L-L of the structure to which microelectrodes (402, 404) are mounted. While microelectrodes (402, 404) are rectangular in the present example, microelectrodes (402, 404) may instead have any other suitable shape. Various other suitable shapes will be apparent to those skilled in the art in view of the teachings herein.

The inventors have determined that any arrangement of electrodes that would reduce or virtually remove fractionated signals, without signal processing applied to the sensed signals, may require the pair of electrodes to conform to the following empirical rules: (1) the length (L) of the electrode must always be at least the same as the spacing gap (Lg) between the pair of electrodes, and (2) the ratio of the area of the spacing gap (Ag) to the area of one electrode (Ae) must be less than or equal to 1. In short hand, this can be restated as: (1) L≥Lg and (2) Ag/Ae≤1. Various permutations of the electrode and gap configurations that may achieve the reduced signal fractionation (without signal processing) can be seen in Table 1. In Table 1, electrodes and gaps that conform to the first and second aspect ratios may reduce or virtually eliminate fractionated signals, without the use of signal processing.

TABLE 1

| Electrode Width (mm) | Electrode Length L (mm) | Electrode Area (Ae in mm²) | Gap length Lg (mm) | Area of Gap (Ag in mm²) | 1st Aspect Ratio (L/Lg) | 2nd Aspect Ratio (Ag/Ae) |
|---|---|---|---|---|---|---|
| 0.8 | 0.1 | 0.08 | 0.1 | 0.08 | 1 | 1 |
| 0.8 | 0.3 | 0.24 | 0.2 | 0.16 | 1.5 | 0.67 |
| 0.8 | 0.5 | 0.4 | 0.1 | 0.08 | 5 | 0.2 |
| 0.8 | 0.5 | 0.4 | 0.2 | 0.16 | 2.5 | 0.4 |
| 0.8 | 0.5 | 0.4 | 0.5 | 0.4 | 1 | 1 |
| 1 | 0.5 | 0.5 | 0.1 | 0.1 | 5 | 0.2 |
| 1 | 0.5 | 0.5 | 0.2 | 0.2 | 2.5 | 0.4 |
| 1 | 0.5 | 0.5 | 0.5 | 0.5 | 1 | 1 |
| 1 | 1 | 1 | 0.1 | 0.1 | 10 | 0.1 |
| 1 | 1 | 1 | 0.2 | 0.2 | 5 | 0.2 |
| 1 | 1 | 1 | 0.5 | 0.5 | 2 | 0.5 |

The sensing and recording of electrocardiogram signals by the inventive electrode configurations are advantageous in that no special signal processing other than conventional low and high pass filters (obvious to those skilled in the art) need to be applied in order to present the electrocardiogram that has little or virtually no fractionated or far-field signals. It is believed that signal processing to reduce or eliminate far-field signals from sensed electrocardiogram are based on certain exclusion criteria that may not be applicable to the sensed signals and therefore the post-processed signal may not be an accurate representation of the signals locally produced by the cardiac tissue.

By way of further example only, the surface area of each microelectrode (402, 404) may be approximately 0.4 squared millimeter or less; any surface area from approximately 0.05 squared millimeter to approximately 0.4 squared millimeter; any surface area from approximately 1 squared millimeter to approximately 0.4 squared millimeter. As used herein, the term "area" or "surface area" is the amount of unit squares (in a suitable dimensional unit, e.g., millimeter) that can be contained or fitted within a two-dimensional planar boundary of the electrode. The term "area" or "surface area" excludes any meaning associated with "surface roughness"; "surface texture"; "fractal surface area"; or any measurement relating to a surface profile or fractals of such area. As well, where the electrode is rolled or crimped onto a non-planar substrate, the area (or surface area) of the electrode is the area unrolled into a planar shape in two-dimension. And where the electrode includes a three-dimensional configuration, the relevant "area" or "surface area" of such electrode is the planar surface in direct physical contact with the cardiac tissue.

By way of example only for a rectilinear electrode, the length (L) of each microelectrode (402, 404) may be any length from approximately 100 microns to approximately 1 millimeter; any length from approximately 100 microns to approximately 300 microns; any length from approximately 300 microns to approximately 500 microns; or any length from approximately 500 microns to approximately 1 mm.

By way of example only for rectilinear electrode, the width (W) of each microelectrode (402, 404) may be any width from approximately 800 microns to approximately 1 mm; any width from approximately 800 microns to approximately 0.5 mm.

By way of further example only, the gap distance (Lg) of each microelectrode (402, 404) may be any distance from approximately 50 microns to approximately 1 mm; any distance from approximately 50 microns to approximately 0.5 mm.

In one version, such as shown schematically in FIG. 13A, each electrode of the electrode pair has a generally rectangular configuration with a dimension (width W) of about 800 microns as measured along the microelectrodes' longitudinal axis Le-Le (or as measured perpendicular to the longitudinal axis L-L) and a longitudinal dimension (length L) generally parallel to the axis L-L of about 300 microns to provide for one electrode surface area of about 0.24 squared-mm and a gap length (Lg) as measured between two nearest surfaces (402a, 404a) of respective microelectrodes. In other words, the gap length (Lg) can be seen as being generally perpendicular to the microelectrodes' longitudinal axis Le-Le (or generally parallel to the longitudinal axis L-L) of about 200 microns with a gap width being the same as the electrode width W for a gap surface area of about 160 microns.

Figure 13C:
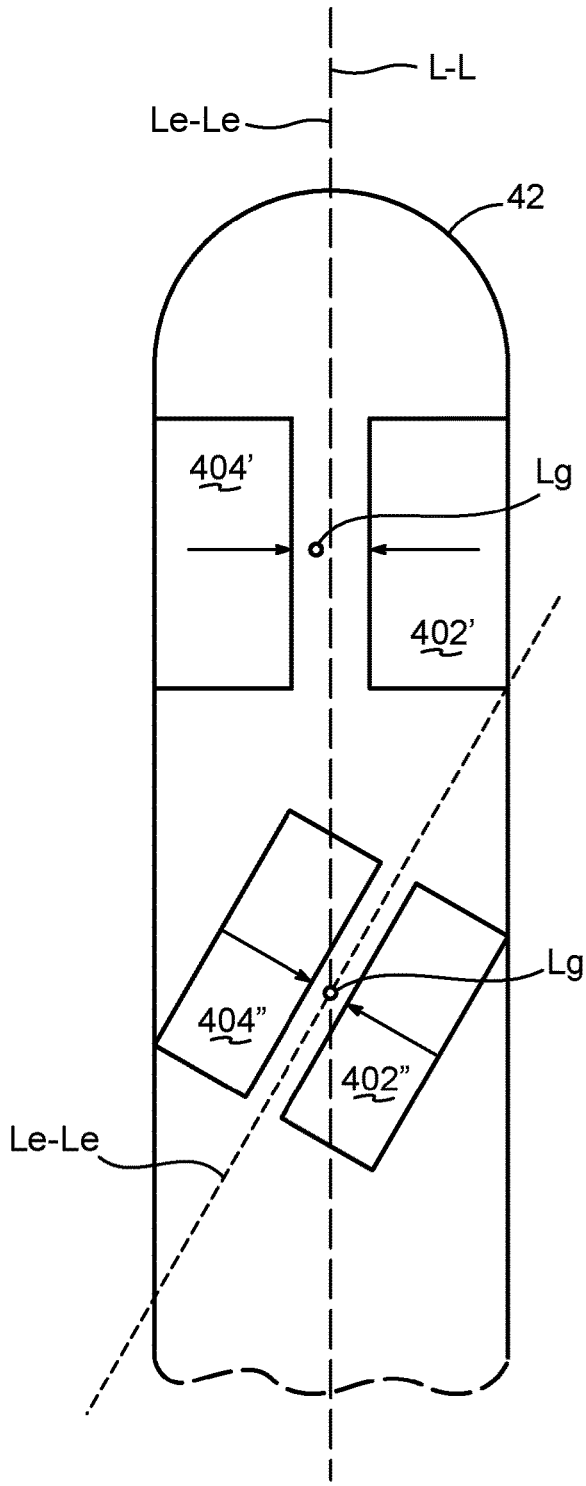
FIG. 13C depicts a schematic plan view of another example of an electrode configuration that may be incorporated into an end effector of the mapping catheter assembly of FIG. 1.
Figure 13D:
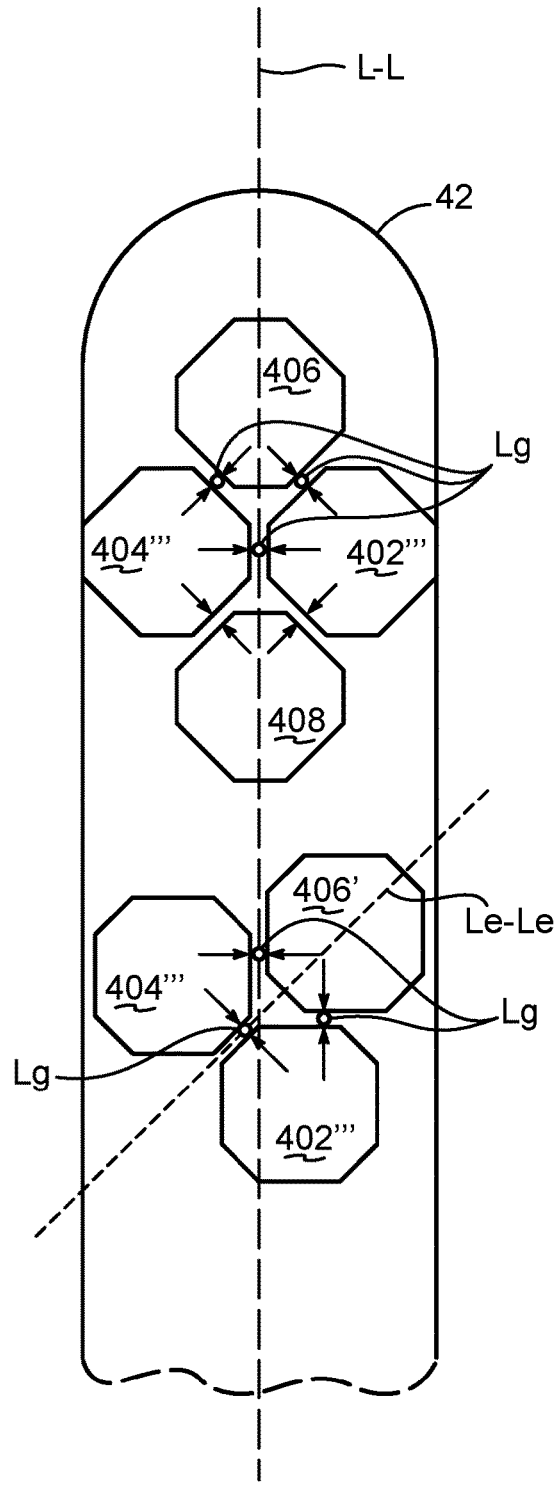
FIG. 13D depicts a schematic plan view of another example of an electrode configuration that may be incorporated into an end effector of the mapping catheter assembly of FIG. 1.

In an alternative version, the microelectrodes (402, 404) of FIG. 13A can be rotated about 90 degrees such that the microelectrodes' longitudinal axis Le-Le coincides (or parallel) with the longitudinal axis L-L of spine (42) as shown by microelectrodes (402', 404') in FIG. 13C. It should be noted that the orientation of the microelectrodes is not limited to a specific angle longitudinal axis Le-Le relative to the longitudinal axis L-L but can be at any orientation, such as shown for electrode pair (402", 404") or electrode pair (402"', 404"') in FIG. 13D as long as two nearest surfaces of respective microelectrode pair are substantially parallel. In FIG. 13D, we have devised the electrode configuration such that the electrodes satisfy the empirical rule that the electrodes can be of any orientation (and number of electrodes) as long as at least two nearest surfaces of respective microelectrodes are substantially parallel with the gap distance Lg between the generally parallel surfaces. Specifically, for each group of electrodes, there can be at least two nearest surfaces that are generally in parallel to arrive at the gap Lg. For example, with respect to the top group of four electrodes (404''', 406, 402''', 408) in FIG. 13D; electrode (404'') has a surface generally parallel to a surface of electrode (406 or 408) to form a first pair (404'', 406) or second pair (404''', 408) with gap Lg for the first and second pairs; electrode (404''') has a surface generally parallel to surface of electrode (402'') to form a third electrode pair with gap Lg; electrode (406) has a surface generally parallel to electrode (402'') to form the fourth electrode pair. With respect to the bottom group of electrodes in FIG. 13D, electrode (404'') has a surface generally parallel to a surface of electrode (406', 402''') to define gap Lg; electrode (406') has respective surfaces that are generally parallel to respective surfaces of electrode (404'', 402''') to define respective gaps Lg.

In versions where the electrode pair configurations may be in shapes other than rectilinear such as, for example, circular (FIG. 13B), polygons (FIG. 13D), or curvilinear electrodes, a conversion factor CF may be used to determine the appropriate gap distance between the electrodes based on the known planar area of either one of the pair of electrodes. The conversion factor CF may range from about 2 to 0.1 in the inverse of the same root dimensional unit as the planar area of an electrode. In one example, where the planar area of one electrode is about 0.08 squared-mm, the smallest gap distance (Lg) along the longitudinal axis extending through both electrodes can be determined by applying the conversion factor CF (in the inverse of the same root dimensional unit of the area or $mm^{-1}$) to arrive at a gap distance Lg of about 100 microns. In another example where the area of one electrode is 0.24 squared-mm, the conversion factor CF (in the inverse of the same root dimensional unit or $mm^{-1}$) can be 1.25 $mm^{-1}$ or less, giving the range of the smallest gap distance Lg from about 300 microns to about 24 microns. Regardless of the shape of the electrodes, a preferred conversion factor CF is about 0.83 (in the inverse of the same root dimensional unit for the electrode area).

Figure 15:
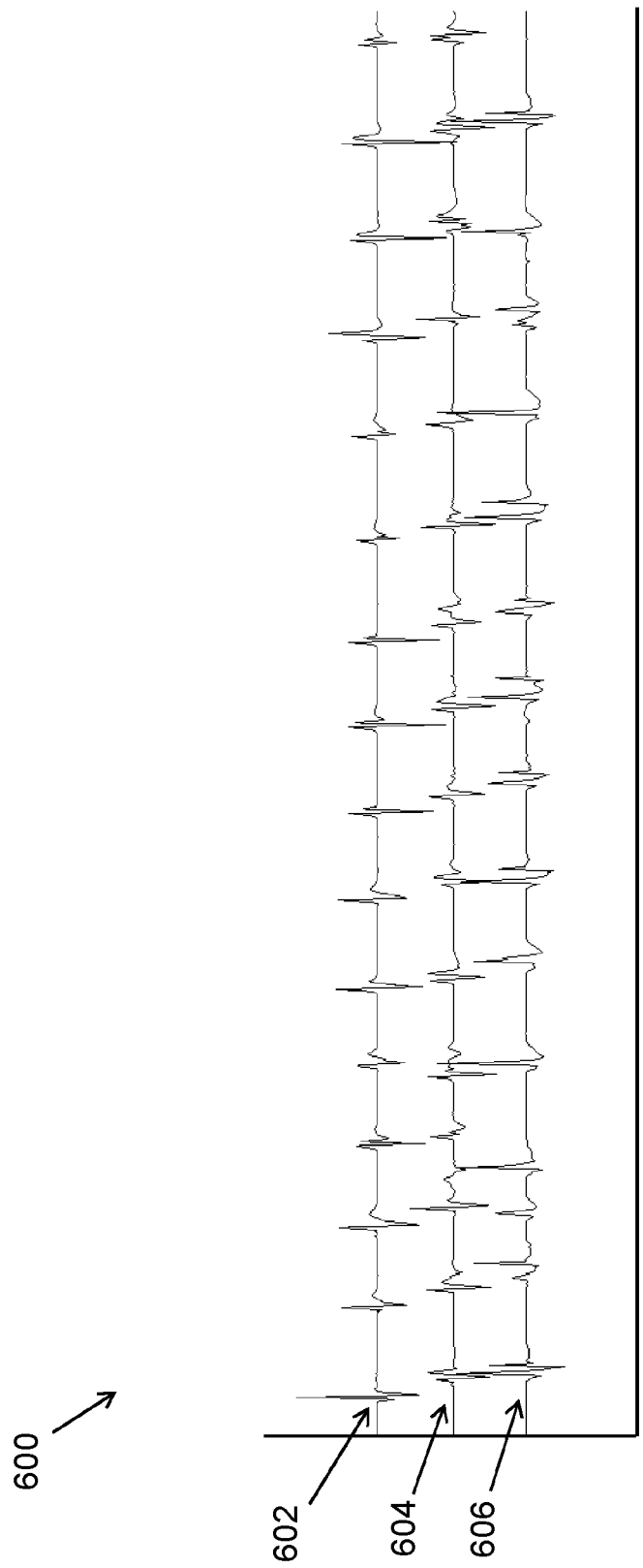
FIG. 15 depicts a plot of electrocardiogram signals without fractionation.

The configurations and arrangements of microelectrodes (402, 404) as described above may prevent microelectrodes (402, 404) from picking up far field electrocardiogram signals (e.g., from the atria), such that microelectrodes (402, 404) only pick up electrocardiogram signals generated by the tissue in contact with microelectrodes (402, 404) (e.g., the pulmonary vein). FIG. 15 shows a graph (600) of three electrocardiogram signal plots (602, 604, 606) that are substantially free of fractionation, representing signals picked up by microelectrodes (402, 404) that are configured and arranged in accordance with the above teachings. Those skilled in the art will understand that plots (602, 604, 606) show voltages over time, as sensed by microelectrodes contacting tissue. By way of example only, plots (602, 604, 606) may represent electrocardiogram signals picked up by three different microelectrode pairs (400) that are positioned within the pulmonary vein of the patient. To the extent that other cardiac structures (e.g., the atria) are generating far field signals with substantial amplitudes, microelectrode pairs (400) are not picking up these far field signals, due to the configuration and arrangement of electrodes (402, 404) in each pair (400) as described above. Instead, the plots (602, 604, 606) show only the potentials from the associated regions of the pulmonary vein itself.

Because these plots (602, 604, 606) of FIG. 15 are free from the kind of fractionation of plots (502, 504, 506) shown in FIG. 14, the physician may more easily annotate the timing of the wavefront and potentially be able to perform a better diagnosis of the direction, source, and cycle length of the wavefront to determine the particular locations within the tissue that are associated with aberrant electrical signals; and may thereby identify the appropriate locations for therapy (e.g., ablation, etc.) with greater certainty and precision. It should be understood that the improvement in the electrocardiogram signals of FIG. 15 over the electrocardiogram signals of FIG. 14 is due solely to the configuration and arrangement of electrodes (402, 404) in each pair (400) as described above. In the present example, the improvement in the electrocardiogram signals of FIG. 15 over the electrocardiogram signals of FIG. 14 is not due to the use of signal filtering algorithms or other signal processing techniques.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a shaft; and (b) an end effector at a distal end of the shaft, wherein the end effector is sized to fit in an anatomical passageway within a subject's cardiovascular system, wherein the end effector comprises at least one electrode pair, wherein the at least one electrode pair is configured to contact cardiovascular tissue and thereby pick up electrocardiogram signals, wherein each electrode pair comprises: (i) a first electrode having a first surface area in a square dimensional unit, and (ii) a second electrode having the first surface area, wherein the first and second electrodes are spaced apart from each other by a gap distance, wherein the gap distance is defined by a multiplication of the first surface area to a conversion factor that ranges from approximately 0.1 to approximately 2 in the inverse of the square root of the same dimensional unit as the first surface area.

Example 2

The apparatus of Example 1, wherein the end effector further comprises a plurality of elongated spines and a plurality of the electrode pairs, wherein the electrode pairs are secured to the spines.

Example 3

The apparatus of Example 2, wherein the shaft defines a longitudinal axis, wherein the spines extend outwardly away from the longitudinal axis, wherein the spines have respective free ends oriented away from the longitudinal axis.

Example 4

The apparatus of Example 2, wherein the spines are configured to bow outwardly and converge distally to form a basket configuration.

Example 5

The apparatus of Example 2, wherein the end effector further comprises an inflatable member, wherein the spines are secured to an outer surface of the inflatable member.

Example 6

The apparatus of any one or more of Examples 1 through 5, wherein the first surface area comprises approximately 0.95 squared millimeters or less.

Example 7

The apparatus of any one or more of Examples 1 through 5, wherein the first surface area comprises approximately 0.4 squared millimeters or less.

Example 8

The apparatus of any one or more of Examples 1 through 7, wherein the gap distance comprises any distance from approximately 50 microns to approximately 3 mm.

Example 9

The apparatus of Example 8, wherein the gap distance comprises any distance from approximately 50 microns to approximately 0.5 mm.

Example 10

The apparatus of any one or more of Examples 1 through 9, wherein the end effector comprises at least one electrode support member associated with the at least one electrode pair, wherein each electrode support member includes a first side and a second side, wherein the electrode pair is presented on only one of the sides of the corresponding electrode support member.

Example 11

The apparatus of any one or more of Examples 1 through 10, wherein the first and second electrode of each electrode pair comprises a bio-compatible metal or conductive polymer.

Example 12

The apparatus of Example 11, wherein the bio-compatible metal comprises a metal selected from one of platinum, palladium, cobalt-chromium, nitinol, gold or any combinations thereof.

Example 13

The apparatus of any one or more of Examples 11 through 12, wherein the bio-compatible metal is coated with iridium oxide.

Example 14

The apparatus of any one or more of Examples 11 through 13, wherein the bio-compatible metal is plasma treated.

Example 15

The apparatus of any one or more of Examples 1 through 14, wherein the at least one electrode pair is configured to pick up electrocardiogram signals of immediate tissue in contact with the electrode pair, without fractionation from far field interactions.

Example 16

The apparatus of any one or more of Examples 1 through 14, wherein the at least one electrode pair is configured to collect electrocardiogram signals of cardiac tissues that the electrode pair is in contact such that the electrocardiogram signals collected by the electrode pair are signals with significantly reduced fractionation during fibrillation of the cardiac tissues.

Example 17

The apparatus of any one or more of Examples 1 through 16, wherein the electrode surface area comprises any surface area from approximately 0.05 squared millimeter to approximately 1 squared millimeter and a gap length ($L_g$) from about 100 microns to about 500 microns.

Example 18

The apparatus of any one or more of Examples 1 through 16, wherein the first surface area comprises any surface area from approximately 0.24 squared millimeter to approximately 0.4 squared millimeter.

Example 19

The apparatus of any one or more of Examples 1 through 18, wherein the end effector is sized to fit in an anatomical passageway within a human cardiovascular system.

Example 20

The apparatus of any one or more of Examples 1 through 19, wherein the first and second electrodes are each rectangular, such that the first surface area is defined by a first length of the first and second electrodes and a first width of the first and second electrodes.

Example 21

The apparatus of Example 20, wherein the electrode pair comprises a configuration other than rectilinear planar shape.

Example 22

The apparatus of any one or more of Examples 20 through 21, wherein the first length comprises any length from approximately 100 microns to approximately 750 microns.

Example 23

The apparatus of any one or more of Examples 20 through 21, wherein the first width comprises any width from approximately 800 microns to approximately 1 mm.

Example 24

The apparatus of any one or more of Examples 20 through 21, wherein the gap distance comprises any distance from approximately 50 microns to approximately 3 mm.

Example 25

The apparatus of any one or more of Examples 20 through 21, wherein the first width comprises any width from approximately 800 microns to approximately 0.5 mm.

Example 26

The apparatus of any one or more of Examples 20 through 25, wherein the gap distance is determined by a product of an area of one electrode up to one millimeter squared and a conversion factor of about 1.25 $mm^{-1}$ or less.

Example 27

The apparatus of Example 26, wherein the conversion factor is about 0.83 $mm^{-1}$.

Example 28

The apparatus of Example 26, wherein the conversion factor is about 0.2 $mm^{-1}$.

Example 29

The apparatus of Example 26, wherein the conversion factor is about 0.4 $mm^{-1}$ in the root dimension of the area of the electrode.

Example 30

The apparatus of Example 26, wherein the conversion factor is about 1 $mm^{-1}$.

Example 31

The apparatus of Example 26, wherein the conversion factor is about 0.5 $mm^{-1}$.

Example 32

The apparatus of any of the preceding claims, wherein the longitudinal axis comprises a longitudinal axis defined by two nearest substantially parallel surfaces of the microelectrodes.

Example 33

An apparatus, comprising: (a) a shaft; and (b) an end effector at a distal end of the shaft, wherein the end effector is sized to fit in an anatomical passageway within a human cardiovascular system, wherein the end effector comprises at least one electrode pair, wherein the at least one electrode pair is configured to contact cardiovascular tissue and thereby pick up electrocardiogram signals, wherein each electrode pair comprises: (i) a first electrode having a first surface area of no greater than approximately 1 squared millimeters, and (ii) a second electrode having a second surface area, wherein the first and second electrodes are spaced apart from each other by a gap distance defined by two nearest substantially parallel surfaces of the respective first and second electrodes, wherein the gap distance (Lg) comprises any value from a product of one of the first surface or second surface area and a conversion factor no greater than about 1.25 $mm^{-1}$.

Example 34

The apparatus of Example 33, wherein the second surface area is equal to the first surface area.

Example 35

The apparatus of any one or more of Examples 33 through 34, wherein the first surface area comprises an area selected from about 0.08 squared millimeter, 0.24 squared millimeter, 0.4 squared millimeter, 0.5 squared millimeter or 1 squared millimeter.

Example 36

The apparatus of any one or more of Examples 33 through 35, wherein the gap distance (Lg) comprises any distance from approximately 50 microns to approximately 500 microns.

Example 37

The apparatus of any one or more of Examples 33 through 35, wherein the gap distance comprises any distance from approximately 100 microns to approximately 200 microns.

Example 38

The apparatus of any one or more of Examples 33 through 37, wherein the first and second electrode comprise generally identical curvilinear planar configuration.

Example 39

The apparatus of any one or more of Examples 33 through 37, wherein the first and second electrode comprise generally identical rectilinear planar configuration.

Example 40

The apparatus of any one or more of Examples 33 through 39, wherein the first width and the gap distance have a ratio of approximately 5:1.

Example 41

An apparatus, comprising: (a) a shaft; and (b) an end effector at a distal end of the shaft, wherein the end effector is sized to fit in an anatomical passageway within a subject's cardiovascular system, wherein the end effector comprises at least one electrode pair, wherein the at least one electrode pair is configured to contact cardiovascular tissue and thereby pick up electrocardiogram signals, each electrode pair includes first and second electrodes spaced apart along a longitudinal axis from each other by a gap area (Ag) located between the electrodes, the gap area (Ag) having a gap length (Lg) with respect to the longitudinal axis such that: (i) a length of one of the electrodes (L) along the longitudinal axis is equal to or greater than the gap length; and (ii) a ratio of an area defined by the gap area (Ag) to one electrode area (Ae) is equal to or less than one.

Example 42

The apparatus of Example 41 in combination with any one or more of Examples 2 through 32.

IV. Miscellaneous

In some versions, end effector (15, 117, 200, 300) is configured to provide RF ablation in addition to providing EP mapping functionality. In some such versions, end effector (15, 117, 200, 300) includes additional electrodes that are dedicated to providing RF ablation. Such RF ablation capabilities may be provided in accordance with the teachings of any of the various patent references cited herein. Alternatively, RF ablation capabilities may be omitted from end effector (15, 117, 200, 300).

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a shaft; and
   (b) an end effector at a distal end of the shaft, the end effector being sized to fit in an anatomical passageway within a subject's cardiovascular system, the end effector comprising at least one electrode pair, the at least one electrode pair being configured to contact cardiovascular tissue and thereby pick up electrocardiogram signals, each electrode pair including first and second electrodes spaced apart along a longitudinal axis from each other by a gap area (Ag) located between the electrodes, the gap area (Ag) having a gap distance (Lg) with respect to the longitudinal axis such that:
   (i) a length of one of the electrodes (L) along the longitudinal axis is equal to or greater than the gap distance (Lg); and
   (ii) a ratio of an area defined by the gap area (Ag) to one electrode area (Ae) is equal to or less than one,
   the gap distance (Lg) being determined by a product of the one electrode area (Ae) up to one millimeter squared and a conversion factor of about 1.25 $mm^{-1}$ or less.

2. The apparatus of claim 1, the end effector further comprising a plurality of elongated spines and a plurality of the electrode pairs, the electrode pairs being secured to the spines.

3. The apparatus of claim 1, the one electrode area (Ae) comprising approximately 0.95 squared millimeters or less.

4. The apparatus of claim 1, the gap distance comprising any distance from approximately 50 microns to approximately 3 mm.

5. The apparatus of claim 1, the end effector comprising at least one electrode support member associated with the at least one electrode pair, each electrode support member including a first side and a second side, the electrode pair being presented on only one of the sides of the corresponding electrode support member.

6. The apparatus of claim 1, the first and second electrode of each electrode pair comprising a bio-compatible metal or conductive polymer.

7. The apparatus of claim 6, the bio-compatible metal comprising a metal selected from one of platinum, palladium, cobalt-chromium, nitinol, gold or any combinations thereof.

8. The apparatus of claim 6, the bio-compatible metal being coated with iridium oxide.

9. The apparatus of claim 1, the at least one electrode pair being configured to pick up electrocardiogram signals of immediate tissue in contact with the electrode pair, without fractionation from far field interactions.

10. The apparatus of claim 1, the one electrode area (Ae) comprising any surface area from approximately 0.05 squared millimeter to approximately 1 squared millimeter and the gap distance (Lg) being from about 100 microns to about 500 microns.

11. The apparatus of claim 1, the one electrode area (Ae) comprising any surface area from approximately 0.24 squared millimeter to approximately 0.4 squared millimeter.

12. The apparatus of claim 1, the first and second electrodes each being rectangular, such that the first surface area is defined by a first length of the first and second electrodes and a first width of the first and second electrodes.

13. The apparatus of claim 12, the first length comprising any length from approximately 100 microns to approximately 750 microns.

14. The apparatus of claim 12, the first width comprising any width from approximately 800 microns to approximately 1 mm.

15. An apparatus, comprising:
(a) a shaft; and
(b) an end effector at a distal end of the shaft, the end effector being sized to fit in an anatomical passageway within a human cardiovascular system, the end effector comprising at least one electrode pair arranged along a longitudinal axis, the at least one electrode pair being configured to contact cardiovascular tissue and thereby pick up electrocardiogram signals, each electrode pair comprising:
 (i) a first electrode having a first surface area of no greater than approximately 1 squared millimeters, the first surface area being defined by a first length of the first electrode extending along the longitudinal axis and a first width of the first electrode extending perpendicular to the longitudinal axis, and
 (ii) a second electrode having a second surface area, the second surface area being defined by a second length of the second electrode extending along the longitudinal axis and a second width of the second electrode extending perpendicular to the longitudinal axis,
the first and second electrodes being spaced apart from each other by a gap distance (Lg) defined by two nearest substantially parallel surfaces of the respective first and second electrodes,
the gap distance (Lg) comprising any value from a product of one of the first surface area or second surface area and a conversion factor no greater than about 1.25 $mm^{-1}$.

16. The apparatus of claim 15, the second surface area being equal to the first surface area.

17. The apparatus of claim 15, the gap distance (Lg) comprising any distance from approximately 50 microns to approximately 500 microns.

18. The apparatus of claim 15, a first width of at least one of the first or second electrodes and the gap distance having a ratio of approximately 5:1.

19. A method of manufacturing the apparatus of claim 1, the method comprising:
(a) selecting the gap distance (Lg) and the length of the one of the electrodes (L) based on a first requirement that the length of the one of the electrodes (L) along the longitudinal axis is equal to or greater than the gap distance (Lg); and
(b) selecting the area defined by the gap area (Ag) and the one electrode area (Ae) based on a second requirement that the ratio of the area defined by the gap area (Ag) to one electrode area (Ae) is equal to or less than one.

* * * * *